(12) United States Patent
Yoshida et al.

(10) Patent No.: US 11,944,478 B2
(45) Date of Patent: Apr. 2, 2024

(54) X-RAY FLUOROSCOPIC IMAGING APPARATUS

(71) Applicant: SHIMADZU CORPORATION, Kyoto (JP)

(72) Inventors: Koki Yoshida, Kyoto (JP); Fumiaki Tanaka, Kyoto (JP); Ryusuke Watanabe, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 151 days.

(21) Appl. No.: 17/543,047

(22) Filed: Dec. 6, 2021

(65) Prior Publication Data

US 2022/0233158 A1    Jul. 28, 2022

(30) Foreign Application Priority Data

Jan. 22, 2021 (JP) ................................. 2021-008695

(51) Int. Cl.
*A61B 6/00* (2006.01)

(52) U.S. Cl.
CPC ............ *A61B 6/487* (2013.01); *A61B 6/4441* (2013.01); *A61B 6/547* (2013.01)

(58) Field of Classification Search
CPC ........ A61B 6/487; A61B 6/4441; A61B 6/547
See application file for complete search history.

(56) References Cited

U.S. PATENT DOCUMENTS

| | | |
|---|---|---|
| 2006/0198497 A1 | 9/2006 | Gotoh |
| 2007/0140437 A1 | 6/2007 | Gotoh |
| 2007/0297574 A1 | 12/2007 | Gotoh |
| 2012/0087469 A1* | 4/2012 | Masuo ................. A61B 6/4441 378/115 |

FOREIGN PATENT DOCUMENTS

| | | |
|---|---|---|
| JP | 2006-239126 A | 9/2006 |
| JP | 2015-116365 A | 6/2015 |
| WO | WO 2007/091295 A1 | 8/2007 |

OTHER PUBLICATIONS

JP 2021-008695, Notification of Reasons for Refusal dated Dec. 7, 2023, 4 pages—Japanese, 4 pages—English.

* cited by examiner

*Primary Examiner* — Dani Fox
(74) *Attorney, Agent, or Firm* — Andrew F. Young, Esq.; NOLTE LACKENBACH SIEGEL

(57) ABSTRACT

An X-ray fluoroscopic imaging apparatus reduces the number of memory switches and performs an auto-positioning for a larger number of rotation positions. The apparatus includes a C-arm 9 supporting the X-ray tube 5 and the X-ray detector 7 face to be rotatable around two axes orthogonal to each other. A rotation position memory storage element 61 stores the rotation position information of the C-arm 9 in correspondence with any of memory switches 55; and a touch panel 43 displays the rotation position information stored in correspondence with selected memory switches 55. The rotation position memory storage element 61 stores a plurality of rotation position information corresponding to the respective memory switches 55, and the touch panel 43 displays any of the plurality of rotation position information stored in correspondence with the memory switches 55 in a predetermined display manner.

6 Claims, 27 Drawing Sheets

FIG. 8

| Switch in correspondence | Corresponding memory | Registered rotation position of C-arm | Rotation direction/Rotation Angle | | | |
|---|---|---|---|---|---|---|
| | | | Body axis direction | | Body axis circumference | |
| | | | CRA | CAU | LAO | RAO |
| Center switch | Memory 66 | Rotation position F0 | 0° | 0° | 0° | 0° |
| Memory switch 55a | First memory 63a | Rotation position F1 | 30° | --- | 30° | --- |
| | Second memory 64a | Rotation position F2 | 25° | --- | 20° | --- |
| | Third memory 65a | Rotation position F3 | 10° | --- | 50° | --- |
| Memory switch 55b | First memory 63b | Rotation position F4 | 0° | 0° | 30° | --- |
| | Second memory 64b | Rotation position F5 | 0° | 0° | 15° | --- |
| | Third memory 65b | Rotation position F6 | 0° | 0° | 40° | --- |
| Memory switch 55c | First memory 63c | Rotation position F7 | --- | 30° | 30° | --- |
| | Second memory 64c | Rotation position F8 | --- | 20° | 45° | --- |
| | Third memory 65c | Rotation position F9 | --- | 30° | 20° | --- |
| Memory switch 55d | First memory 63d | Rotation position F10 | 30° | --- | 0° | 0° |
| | Second memory 64d | Rotation position F11 | 10° | --- | 0° | 0° |
| | Third memory 65d | Rotation position F12 | 45° | --- | 0° | 0° |
| Memory switch 55e | First memory 63e | Rotation position F13 | --- | 30° | 0° | 0° |
| | Second memory 64e | Rotation position F14 | --- | 15° | 0° | 0° |
| | Third memory 65e | Rotation position F15 | --- | 60° | 0° | 0° |
| Memory switch 55f | First memory 63f | Rotation position F16 | 30° | --- | --- | 30° |
| | Second memory 64f | Rotation position F17 | 20° | --- | --- | 20° |
| | Third memory 65f | Rotation position F18 | 40° | --- | --- | 40° |
| Memory switch 55g | First memory 63g | Rotation position F19 | 0° | 0° | --- | 30° |
| | Second memory 64g | Rotation position F20 | 0° | 0° | --- | 60° |
| | Third memory 65g | --- | --- | --- | --- | --- |
| Memory switch 55h | First memory 63h | Rotation position F21 | --- | 30° | --- | 30° |
| | Second memory 64h | --- | --- | --- | --- | --- |
| | Third memory 65h | --- | --- | --- | --- | --- |
| Memory switch 57a | Short term memory 67a | Rotation position F22 | 25° | --- | 20° | |
| Memory switch 57b | Short term memory 67b | --- | --- | --- | --- | --- |
| Memory switch 57c | Short term memory 67c | --- | --- | --- | --- | --- |

X-RAY FLUOROSCOPIC IMAGING APPARATUS

CROSS REFERENCE TO RELATED APPLICATION

This application relates to, and claims priority from, Ser. No.: JP2021-008695 filed Jan. 22, 2021, the entire contents of which are incorporated herein by reference.

FIGURE FOR PUBLICATION

FIG. 3.

BACKGROUND OF THE INVENTION

Field of the Invention

The present invention relates to an X-ray fluoroscopic imaging apparatus that performs an X-ray imaging in multiple directions by rotating the X-ray tube and the X-ray detector in the body axis direction and around the body axis of a subject while being supported to be facing each other.

Description of the Related Art

When a procedural operation or a medical examination using a catheter procedure is performed in the medical field, e.g., in a circulatory field including such as cardiovascular disorder, the X-ray fluoroscopic imaging apparatus that performs an X-ray fluoroscopy or an X-ray imaging is now mandatory. In such a procedural operation, the fluorescence imaging is performed by irradiating the circulatory region of the subject with the X-ray in an arbitrary direction. The operator performs the procedural operation by operating the arbitrarily the catheter referring to the X-ray image data acquired using the fluoroscopic imaging.

The X-ray fluoroscopic imaging apparatus comprises an imaging system consisting of a table on which the subject is loaded, an X-ray tube and an X-ray detector and a C-shape arm (C-arm) supporting the imaging system. The X-ray tube and the X-ray detector are installed to one end and the other end respectively of the C-arm and the C-ram is set to allow the X-ray tube and the X-ray detector to face each other while sandwiching the subject. The C-arm is rotatable in the body axis direction and the circumference direction of the body axis of the subject (here in after "rotation direction") with a predetermined rotation angle. The C-arm enables rotating to an arbitrary rotation position (in the arbitrary rotation direction and with the arbitrary angle), so that the X-ray imaging can be performed from multiple directions relative to the target region (region of interest) of the subject.

It is disclosed that a conventional X-ray fluoroscopic imaging apparatus has a function (auto-positioning function) with which the predetermined rotation position is linked to the memory switch and stored therein, and the C-arm thereof is shifted to such a memorized rotation position at an arbitrary timing (e.g., refer to the Patent Document) 1). The conventional X-ray fluoroscopic imaging apparatus having the auto-positioning function comprises a console equipped with a memory execution switch, a rotation execution switch and a plurality of memory switches.

For example, the operation in which the rotation position is memorized in correspondence with the memory switch runs pushing down the first memory switch and then memory execution switch in the state in which the C-arm is being shifted to the predetermined rotation position. In accordance with the operation of the memory execution switch, the information of the rotation position of the C-arm at the present time is stored while linking to the first memory switch. And the information of the respective different rotation positions with regard to a plurality of memories is stored while linking thereto for a long period of time by running the same operation on the second memory switch and subsequently therefrom.

When the C-arm is shifted to the desired rotation position, the C-arm automatically shifts due to the operation of the rotation execution switch following selecting and then pushing down the memory switch linked to the information of such a rotation position. The C-arm can be quickly rotated to a plurality of rotation positions corresponding to the number of the memory switches due to such an auto-positioning function.

RELATED PRIOR ART

Patent Document

Patent Document 1—WO 2007/091295 A1

ASPECTS AND SUMMARY OF THE INVENTION

Objects to be Solved

Nevertheless, in the case of a conventional example having such structure, following problems are remained to be solved.

As a recent trend, the C-arm is shifted to a number of the rotation positions when proceeding the procedural operation and the X-ray images are acquired by irradiating X-rays from a number of rotation positions. In addition, as a trend, the procedural operations is performed for a larger number of the subjects using the X-ray fluoroscopic imaging apparatus. As a result, the number of rotation positions to be stored would become vast.

According to the conventional X-ray fluoroscopic imaging apparatus, the number of memory switches corresponding to the number of rotation positions to be stored is needed. Therefore, provided the number of rotation positions to be stored becomes vast, the number of the memory switches becomes also vast. Whereas the scope of the operation board is limited, and it is difficult that a vast number of the memory switches are in place on the operation board, accordingly. On the other hand, it is ideal to make the respective memory switches smaller to place the vast number of the memory switches on the operation board, but the memory switch should have the size larger than a certain size while considering operability of the memory switch. Accordingly, a support with miniaturization of the memory switch is limited.

The present invention is accomplished considering such circumstances and the object of the present invention is to provide an X-ray fluoroscopic imaging apparatus capable of suppressing increase of the number of memory switches and performing an auto-positioning for a larger number of rotation positions.

Means for Solving the Problem

The present invention constitutes the following structure to achieve such a purpose.

Specifically, the X-ray fluoroscopic imaging apparatus of the present invention comprises: an X-ray tube that irradiates an X-ray to a subject; an X-ray detector that is in place to face the X-ray tube and detects the X-ray transmitting the subject; a support mechanism that supports the X-ray tube and the X-ray detector while facing each other and is rotatable around the respective two axes that are orthogonal to each other; a rotation position detection element that detects information related to a rotation direction and a rotation angle around the respective axes of said support mechanism as a rotation position information; a plurality of memory switches; a rotation position memory storage element that stores said rotation position information in correspondence with any of said memory switches; a rotation position display element that displays said rotation position information that is stored in correspondence with such memory switches selected by selecting any of said memory switches; and a rotation instruction element that rotates the support mechanism in the rotation direction and with the rotation angle in correspondence with the rotation position information that are displayed on the rotation position information display element; wherein the rotation position memory element is configured to store a plurality of rotation position information in correspondence with the respective memory switches, and the rotation position information display element is configured to display in a predetermined display manner any of the plurality of rotation position information stored in correspondence with the memory switch by which the memory switch is operated in a predetermined manner.

In such a configuration, the rotation position information display element, a plurality of memory switches, the rotation position memory storage element and the rotation instruction element. The rotation position memory storage element stores the rotation position information of the support mechanism in correspondence with any of the memory switches and is configured to store a plurality of rotation position information corresponding to the respective memory switches. Specifically, every single memory switch is configured to be stored in correspondence with a plurality of rotation positions. Therefore, while cutting the number of the memory switches installed to the X-ray fluoroscopic imaging apparatus, a larger number of the rotation position information can be stored in correspondence with the memory switches.

The rotation position information display element displays the rotation position information that is stored in correspondence with such selected memory switches due to the selection of any of the memory switches. Further, the rotation position information display element is configured to display any of the plurality of rotation position information stored in correspondence with such memory switches in the predetermined manner due to operation of the memory switches in the predetermined manner. Specifically, the information of the respective rotation positions can be selectively read out and displayed corresponding to the operation manner of the memory switch due to the configuration in which a plurality of the rotation positions is stored in correspondence with one memory switch.

And the support mechanism can be rotated in the rotation direction and with the rotation angle respectively corresponding to the rotation position information that is displayed on the rotation position information display element due to the operation of the rotation instruction element. Accordingly, an operation is now achievable, wherein the support mechanism is rotated to such a rotation position by selecting the one rotation position from a plurality of stored rotation positions with regard to the configuration in which the plurality of the rotation positions are stored in correspondence with one memory switch.

According to the present invention set forth above, it is preferable that the respective memory switches is in place in the position corresponding to the rotation direction stored in correspondence with the memory switch on the basis of the base (reference) region indicating the position of the subject.

[Action and Effect] With regard to the X-ray fluoroscopic imaging apparatus according to the present invention, the position, at which the respective memory switches are in place on the basis of the reference region, is defined so as to correspond to the direction of the rotation position stored in correspondence with the memory switches.

According to such a configuration, based on the position at which the memory switches are in place on the basis of the reference region, the operator can intuitively understand that the rotation position stored in correspondence with such memory switches is in any direction on the basis of the reference region. Therefore, the time needed for the auto-positioning operation can be reduced, and an incident of an error operation during the auto-positioning operation can be absolutely avoided.

The present invention may constitute the following structure to achieve such a purpose.

Specifically, the X-ray fluoroscopic imaging apparatus of the present invention comprises: an X-ray tube that irradiates an X-ray to a subject; an X-ray detector that is in place facing said X-ray tube detects said X-ray transmitting said subject; a support mechanism that supports said X-ray tube and said X-ray detector so as to face each other and is rotatable around respective two axes that are orthogonal to each other; a rotation position detection element that detects information of a rotation direction and a rotation angle around each axis of the support mechanism as a rotation position information; a rotation position memory storage element that stores a plurality of memory switches and the rotation position information in correspondence with any of the memory switches; a rotation position display element that displays the rotation position information that is stored in correspondence with the memory switch selected by selecting any of the memory switches; and a rotation instruction element that rotates the support mechanism in the rotation direction and with the rotation angle in correspondence with the rotation position information that is displayed on the rotation position information display element; a rotation position information erasing element that erases said rotation position information stored in correspondence with said respective memory switches due to an operation instructing a predetermined specific process of a series of examination processes relative to said subject as a trigger

[Action and Effect] The X-ray fluoroscopic imaging apparatus, according to the present invention, comprises the rotation position information display element, the plurality of memory switches, the rotation position memory storage element, the rotation instruction element and the rotation position information erasing element. The rotation position memory storage element stores the rotation position information of the support mechanism in correspondence with any of the memory switches. The rotation position information display element displays the rotation position information that is stored in correspondence with such memory switches selected by selecting any of memory switches. And the support mechanism is rotated in the rotation direction and with the rotation angle respectively corresponding to the rotation position information displayed on the rotation position information display element due to the operation of the rotation instruction element. According to the auto-positioning operation using such a configuration, the X-ray fluoroscopic imaging condition can be reproduced by re-shifting the support mechanism to such a rotation position during performing the procedural operation relative to the subject following storing the rotation position information of the support mechanism in correspondence with the memory switches.

And once the operation for instructing a specific predetermined process of a series of examination processes relative to the subject is performed, the rotation position information erasing element erases the rotation position information stored in correspondence with the respective memory switches due to such an operation as a trigger. According to such a configuration, once a series of examination processes relative to the subject is completed, the rotation position information stored in correspondence with the respective memory switches are automatically erased. In other words, the rotation position information stored in correspondence with the memory switches when the examination is conducted on the subject are stored only during the examination on such a subject.

In such a way, even when a number of rotation positions are needed to be stored since a number of subjects are examined, the information of the rotation positions is erased whenever the examination relative to the subject ends. Therefore, it is not required to forever and continuously store the rotation position information with regard to all subjects in correspondence with the respective individual memory switches. Specifically, the number of the memory switches is limited to the number of the rotation positions to be stored mandatory with regard to the examination relative to each subject. Therefore, while reducing the number of the memory switches installed to the X-ray fluoroscopic imaging apparatus, the examination for a number of subjects can be adequately performed using the auto-positioning operation.

In addition, according to the present invention set forth above, it is preferable that the rotation position memory storing element comprises the memory mode shifting instruction element that executes shifting to the memory mode to store the rotation position information in the memory switches and that the rotation position memory storing element stores the rotation direction and the rotation angle of the support mechanism at the time when the operation is executed in correspondence with the memory switches as the rotation position information by operating any of the memory switches in the shifting state at the memory mode.

[Action and Effect] According to the X-ray fluoroscopic imaging apparatus of the present invention, the rotation position memory storing element stores the rotation direction and the rotation angle of the support mechanism at the time when the operation is executed in correspondence with the memory switches as the rotation position information by operating any of the memory switches. Therefore, the information of such rotation position can be stored by operating the memory switches when it is found that the support mechanism has rotated to the adequate rotation position to be stored. As a specific example, once it is found that the desired X-ray image is obtained by the X-ray fluoroscopic imaging, the rotation position information of the support mechanism at the time when the X-ray image is obtained is automatically stored by operating the memory switches. Specifically, the rotation position information corresponding to the X-ray image imaging condition is exactly and quickly stored, so that the rotation position required to obtain such an X-ray image can be easily and precisely reproduced later.

In addition, according to the present invention, a selected memory switch display mechanism is preferably included to display the latest memory switch operated by the operator among the plurality of memory switches in the different manner from other memory switches thereof.

[Action and Effect] According to the X-ray fluoroscopic imaging apparatus of the present invention, the selected memory switch display mechanism displays the latest memory switch operated by the operator in the different manner from other memory switches thereof. In such a configuration, the operator can absolutely identify the memory switch operated right before among the plurality of the memory switches, i.e., such a memory switch is a selection object for the auto-positioning operation at the present time. Therefore, an erroneous operation in the auto-positioning operation can be avoided, and the time needed for such an operation can be further shortened.

Effects of the Present Invention

According to the first aspect of the X-ray fluoroscopic imaging apparatus of the present invention, the rotation position memory storage element stores the rotation position information of the support mechanism in correspondence with any of the memory switches and is configured to store a plurality of rotation position information corresponding to the respective memory switches. Specifically, every single memory switch is configured to be stored in correspondence with the plurality of rotation positions. Consequently, while lowering the number of the memory switches installed to the X-ray fluoroscopic imaging apparatus, a larger number of the rotation position information can be stored in correspondence with the memory switches.

According to the second aspect, the rotation position memory storage element stores the rotation position information of the support mechanism in correspondence with any of the memory switches. And once the operation for instructing a specific predetermined process of a series of examination processes relative to the subject is performed, the rotation position information erasing element erases the rotation position information stored in correspondence with the respective memory switches using such an operation as a trigger. Therefore, even when a number of rotation positions are needed to be stored since a number of subjects are examined, the information of the rotation positions is erased whenever the examination relative to the subject ends. Therefore, it is not required to forever and continuously store the rotation position information with regard to all subjects in correspondence with the respective individual memory switches. Therefore, while lowering the number of the memory switches installed to the X-ray fluoroscopic imaging apparatus, the auto-positioning can be performed on a larger number of rotation positions for many subjects.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 8 is a list table illustrating the correspondence between the memory switches and memories and the rotation position information registered in advance in the memory.

FIG. 9A is a flow chart illustrating the auto-positioning operation in the default mode.

FIG. 9B is a flow chart illustrating the operation to register the rotation position information into the first memory switch group in the registration mode.

FIG. 9C is a flow chart illustrating the operation to register the rotation position information in the second memory switch group in the edition mode.

DETAILED DESCRIPTION OF THE PREFERRED EMBODIMENTS

Figure 1:
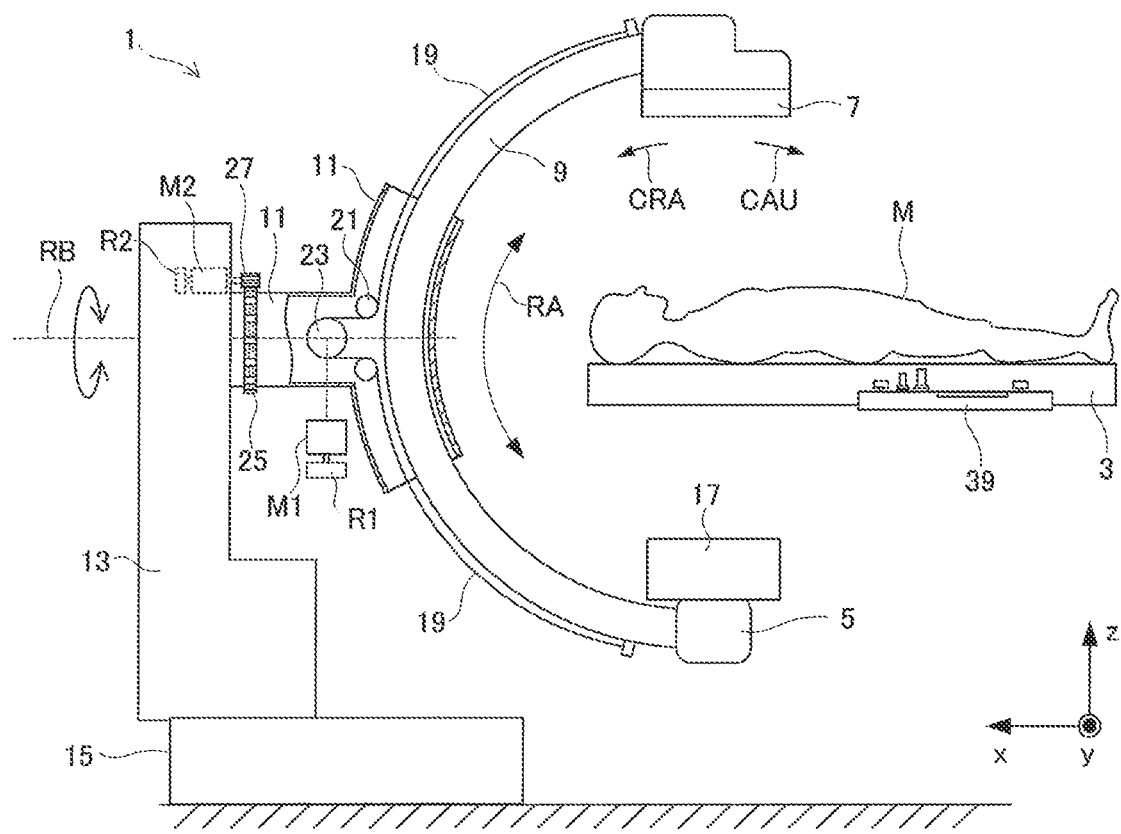
FIG. 1 is a front view illustrating the entire structure of an X-ray fluoroscopic imaging apparatus according to the Embodiment.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Referring to Figures, the inventor sets forth Embodiments of the present invention.

(Illustration of the Entire Structure)

Figure 2:
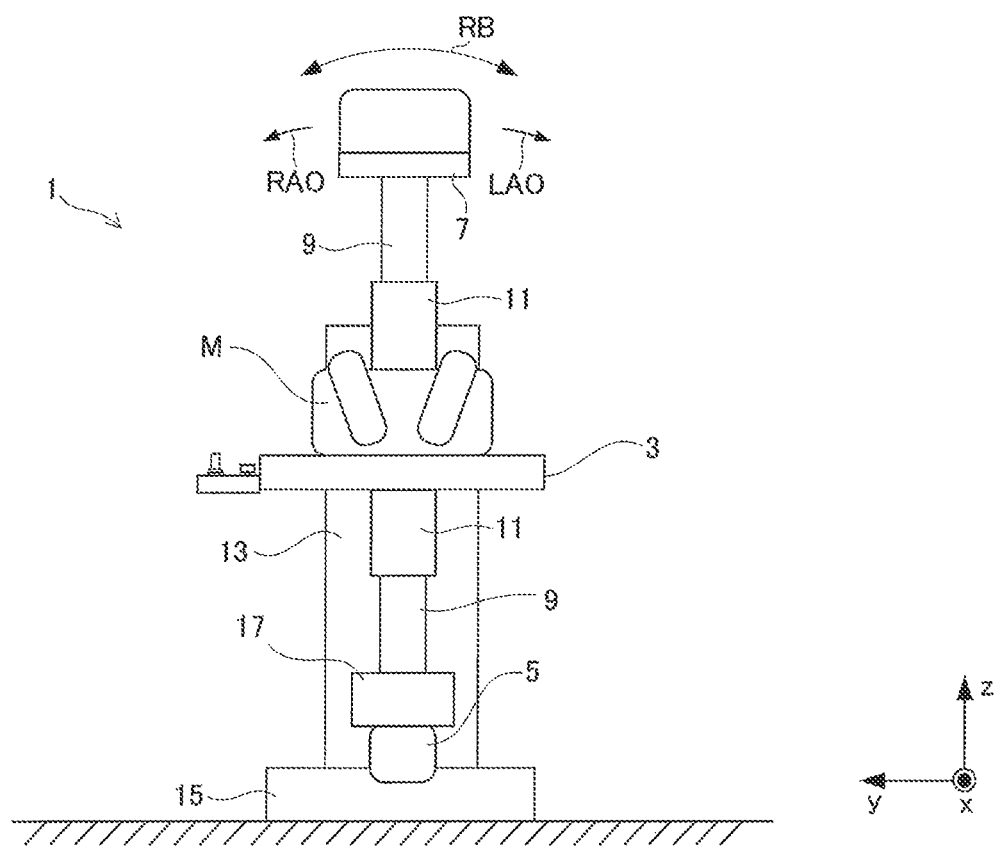
FIG. 2 is a right-side view illustrating the entire structure of the X-ray fluoroscopic imaging apparatus according to the Embodiment.

Referring to FIG. 1 and FIG. 2, the X-ray fluoroscopic imaging apparatus 1 according to the Embodiment comprises an X-ray tube 5 and an X-ray detector 7 which are facing each other while sandwiching the subject M on the table 3 in a supine posture. The X-ray tube 5 irradiates the X-rays to the subject M. The X-ray detector 7 detects and converts the X-ray, which is irradiated from the X-ray tube 5 to the subject M and transmits therethrough, to an electric signal and then outputs the electric signal as an X-ray detection signal. One example of the X-ray detector 7 is such as a flat panel detector (FPD).

The X-ray tube 5 and the X-ray detector 7 are respectively installed to a C-arm 9. The C-arm 9 has an approximately C-like bending shape. The X-ray tube 5 is installed to one end of the C-arm 9 and the X-ray detector 7 is installed to the other end of the C-arm 9. The C-arm 9 that is held by the arm holding member 11 capable of sliding along the circular arc pathway of the C-arm 9 indicated by the sign RA. The C-arm 9 slides in the direction denoted by the sign RA, i.e., rotates around the axis orthogonal to the body axis (hereinafter body axis direction) of the subject M.

The arm holding member 11 that is installed to the side portion of the supporting column 13 is configured to be rotatable around the horizontal axis RB parallel to the x-direction (long side of the fluoroscopy range during the table 3 and also called around the body axis) and body axis direction). The C-arm 9 that is held by the arm holding member 11 rotates around the body axis of the subject M in accordance with rotation of the arm holding member 11.

According to the present Embodiment as set forth above, the C-arm 9 rotates independently around two axes orthogonal to each other (e.g., the body axis direction of the subject M and the circumference direction of the body axis). In addition, the direction consisting of the body axis direction of the subject M and the circumference direction of the body axis thereof is called collectively hereinafter "rotation direction". The C-arm 9 rotates freely and respectively around the orthogonal two axes to each other along the respective arch path RA and arch path RB, so that X-rays can be irradiated to the subject M from arbitrary directions. The C-arm 9 corresponds to the support mechanism of the present invention.

In addition, referring to FIG. 1 and FIG. 2, the state in which the X-ray tube 5 and the X-ray detector 7 are perpendicular relative to the subject M is the initial (default) state of the C-arm 9. And the rotation position of the C-arm 9 in the initial state is defined as the default position of the C-arm 9. With regard to the default position of the C-arm 9, the rotation angle of the C-arm is specified as 0° for the respective body axis direction and circumference direction of body axis.

The support column 13 that is supported by the support pedestal base 15 installed to the floor surface is movable horizontally in the v-direction (short side direction of the table 3). The arm holding member 11 and the C-arm 9 supported by the support column 13 move in the y-direction following the horizontal move of the support column 13. The collimator 17 installed below the X-ray tube 5 limits X-rays irradiated from the X-ray tube 5 to a predetermined shape. An example of the limited shape of the X-ray may be a cone shape like a pyramid.

Next, the inventors set forth the rotation mechanism of the C-arm 9. The rotation of the C-arm 9 in the body axis direction of the subject M is achieved using a driving mechanism inside the arm holding member 11. A part of a belt 19 of which both ends are fixed to the C-ram 9 is housed inside the arm holding member 11, and the belt 19 is bridged with a driving roller 23 through a guide roller 21.

A driving motor M1 and a rotary encoder R1 are attached inside the arm holding member 11. The driving motor M1 rotates the driving roller 23. The rotary encoder R1 detects the rotation direction and rotation of the driving motor M1. The C-arm 9 rotates
  in the body axis direction of the subject M through the belt 19 due to the rotation of the rotation motor M1. In addition, for convenience of explanation, referring to FIG. 1, the driving motor M1 and the rotary encoder R1 are shown outside the arm holding member 11.

The rotation of the C-arm 9 in the circumference direction of the body axis of the subject M is achieved by rotating the arm holding member 11 in the circumference direction of the horizontal axis RB, i.e., the circumference direction of the body axis of the subject M. The pedestal base portion of the arm holding member 11, i.e., the opposite end of the side holding the C-arm 9, is supported with the side portion of the support column 13 so as to be rotatable and a gear 25 is fixed near the support plane.

The gear 25 is occluded with a pinion gear 27, and the pinion gear 27 is mounted on the output shaft of the driving motor M2 installed inside the support column 13. The C-arm 9 rotates in the circumference direction of the body axis of the subject M together with the arm holding member 11 due to rotation of the driving motor M2. The rotary encoder R2 detects the rotation direction and rotation of the driving motor M2.

Figure 3:
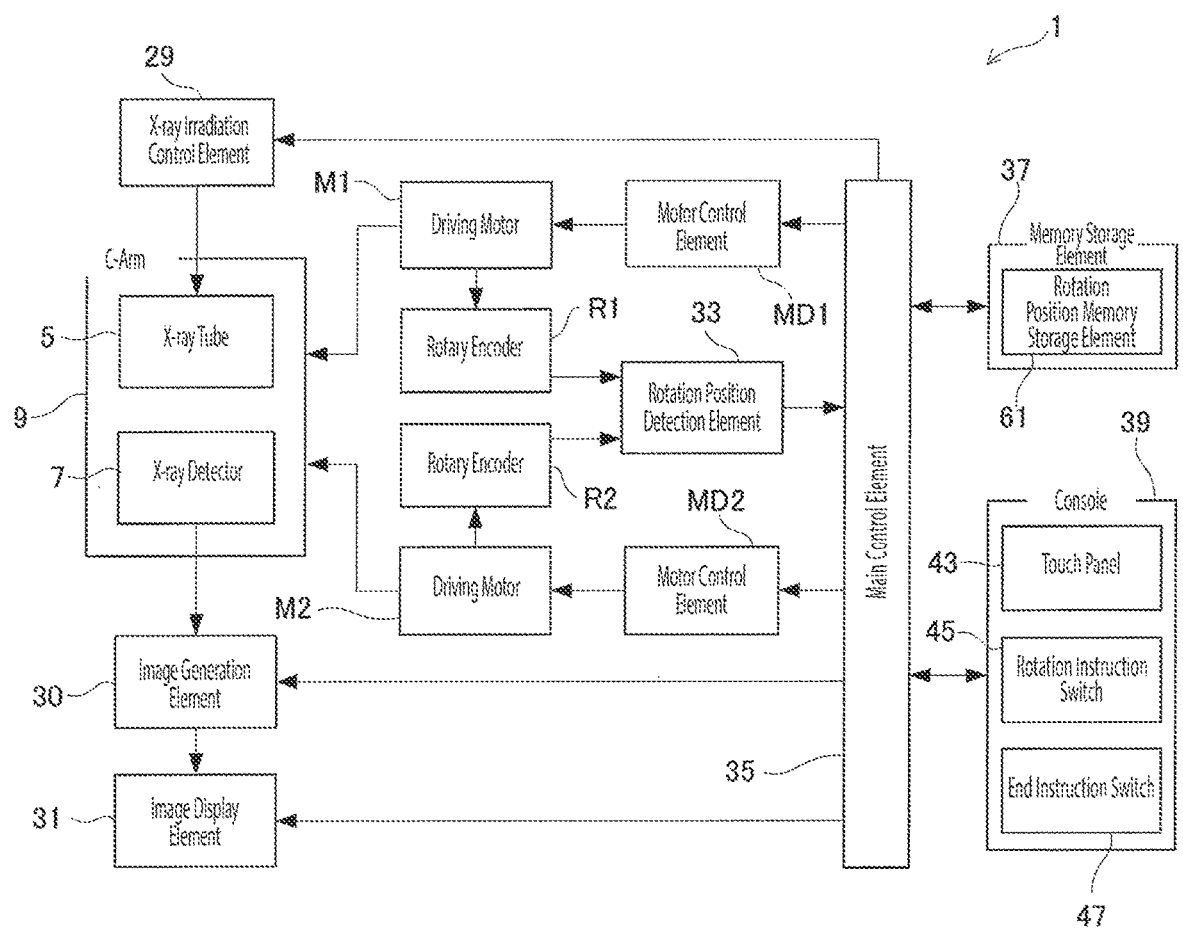
FIG. 3 is a schematic functional block diagram illustrating the X-ray fluoroscopic imaging apparatus according to the Embodiment.

Referring to FIG. 3, the X-ray fluoroscopic imaging apparatus 1 further comprises an X-ray irradiation control element 29, an image generation element 30, an image display element 31, a motor control element MD1, a motor control element MD2, a rotation position detection element 33, a main control element 35, a memory storage element 37 and a console 39. The X-ray irradiation control element 29 is configured to output a high voltage to the X-ray tube 5. And the dose of X-ray irradiated by the X-ray tube 5 and the timing of X-ray irradiation are controlled based on the high voltage output provided by the X-ray irradiation control element 29.

The image generation element 30 that is installed to the latter part of the X-ray detector 7 generates an X-ray image based on the X-ray detection signal output from the X-ray detector 7. The image display element 31 that is installed to the latter part of the image generation element 30 displays the X-ray images generated by the image generation element 30. An example of the image display element 31 is a liquid crystal monitor. As a structural example, the image display element 31 is hanging from ceiling or loaded on a movable wheeled platform.

The motor control element MD1 is installed in the upstream of the driving motor M1 and controls the rotation direction and rotation of the driving motor M1. The motor control element MD2 is installed in the upstream of the driving motor M2 and controls the rotation direction and rotation of the driving motor M2.

The rotation position detection element 33 detects the rotation position of the C-arm 9 based on the rotation direction and rotation of the driving motor M1 detected by the rotary encoder R1 and the rotation direction and rotation of the driving motor M2 detected by the rotary encoder R2. The rotation position of the C-arm 9 is identified according to the rotation direction and rotation of the C-arm 9.

Figure 4:
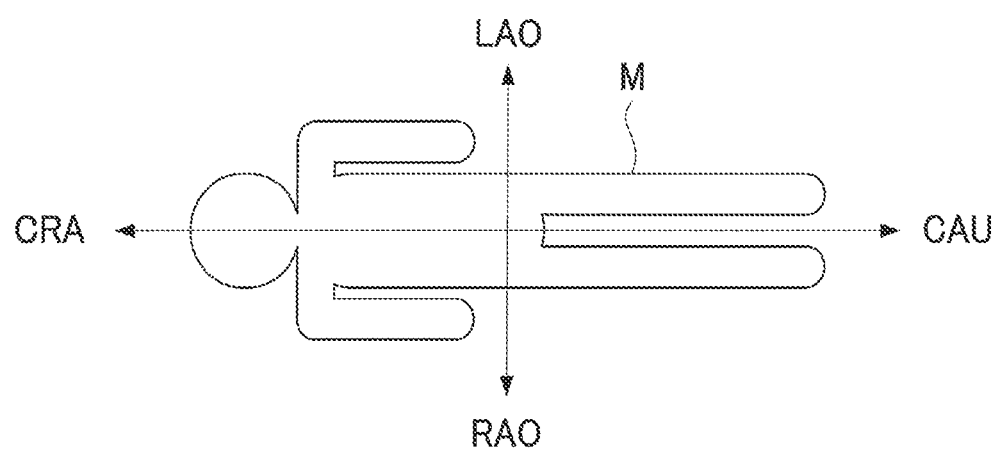
FIG. 4 is a schematic diagram illustrating the rotation direction of the C-arm according to the Embodiment.

The rotation direction of the C-arm 9 is expressed as follows. Referring to FIG. 4, with regard to the body axis direction of the subject M, the head side direction thereof is denoted in CRA (cranial) hereinafter and the foot side direction thereof is denoted in CAU (caudal) hereinafter. And referring to FIG. axis of the subject M, the rotation direction to the left side from the head side direction thereof is denoted in LAO (left anterior oblique) hereinafter and the rotation direction to the right side from the head side thereof is denoted in RAO (right anterior oblique) hereinafter.

The rotation direction of the C-arm 9 is specified by a combination of the rotation direction (CRA or CAU) of the C-arm 9 in the body axis directions of the subject M and the rotation direction (LAO or RAO) of the C-arm 9 in the circumference direction of the subject M. And the rotation angle of the C-arm 9 is specified by a combination of the rotation angle of the C-arm 9 in the body axis directions of the subject M and the rotation angle of the C-arm 9 in the circumference direction of the body axis of the subject M.

A rotation position detection element 33 calculates the rotation direction and rotation angle of the C-arm 9 which rotates in the body axis direction of the subject M based on the information of the rotation direction and rotation of the driving motor M1, which the rotary encoder R1 sends. And the rotation position detection element 33 detects the rotation direction and rotation angle of the C-arm 9 which rotates in the circumference direction of the body axis of the subject M based on the information of the rotation direction and rotation of the driving motor M2, which the rotary encoder R2 sends. And the rotation direction and rotation angle of the C-arm 9 are calculated based on such information.

A main control element 35 comprises an information processing means, such as a central processing unit (CPU) as an example. The main control element 35 controls comprehensively a variety of components of the X-ray fluoroscopic imaging apparatus 1, e.g., the motor control element MD1, the motor control element MD2, the X-ray irradiation control element 29, the image generation element 30 and the image display element 31.

The memory storage element 37 stores a variety of information, e.g., the information as to the X-ray imaging condition including such as the tube voltage and the tube electric current, a variety of X-ray images generated by the image generation element 30 and the information related to the image processing with the image generation element 30 and the rotation position information of the C-arm 9.

A console 39 is used to input the operator's instruction relative to the operation of the X-ray fluoroscopic imaging apparatus 1, and the main control element 35 conducts a comprehensive control following the instruction which the operator inputs using the console 39. Examples of the console 39 includes e.g., a key-board panel, a touch input panel, a mouse, a dial, a change switch and a push button switch.

According to the present Embodiment, referring to FIG. 1, the console 39 is attached to the side portion of the table 3. In such a case, the operator stands near by the table 3 and operates the console 39 while standing. The console 39 is attached to the table 3, so that the operator can perform a variety of operations as for the X-ray fluoroscopic imaging apparatus 1 while performing a catheter procedure or an examination for the subject M.

In addition, the console 39 is not limited to be attached to the side portion of the table 3, and the top plane of the removable wheeled platform may be equipped with the console 39. In addition, the console 39 is not limited to be in place in the long side portion of the table 3, and the console 39 may be attached to the short side portion of the table 3.

Figure 5:
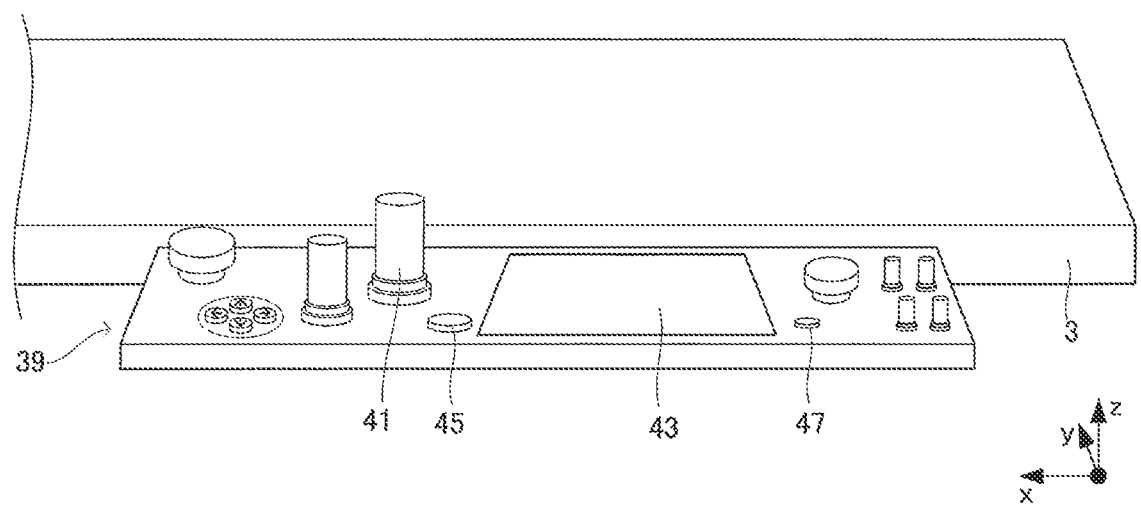
FIG. 5 is a perspective view illustrating an input element according to the Embodiment.

Next, the inventors set forth essential operation devices installed to the console 39. Referring to FIG. 5, the console 39 comprises the arm operation lever 41, the touch panel 43, the rotation instruction switch 45 and the end instruction switch 47.

The arm operation lever 41 is configured to be tiltable back and forth and around and adjusts the rotation position of the C-arm 9. For example, provided the operator grips the arm operation lever 41 and tilts forth, the C-arm 9 rotates in the LAO direction. The rotation angle of the C-arm 9 changes corresponding to the tilt angle of the arm operation lever 41 or the time period of tilting. Further, provided the operator grips the arm operation lever 41 and tilts to the left direction, so that the C-arm 9 rotates in the CRA direction. The operator can manually and finely adjust the rotation position of the C-arm 9 using the arm operation lever 41.

The touch panel 43 runs a such as an operation for storing the rotation position of the C-arm 9 and displays a number of iconic switches. In addition, a plurality of the modes such as an default mode, a registration mode and an edition mode is arbitrarily switched, so that the displayed iconic switch is changed accordingly. The inventors set forth later the structure of the touch panel 43 and a variety of modes. The touch panel 43 corresponds to the rotation position information display element in the present invention.

A rotation instruction switch 45 is a push button switch for moving the C-arm 9 to the predetermined rotation position. Specifically, the C-arm 9 rotates toward such a specific rotation position by pushing down the rotation instruction switch 45 in the state in which the stored specific rotation position is selected using the touch panel 43. The rotation instruction switch 45 corresponds to the rotation instruction element of the present invention.

The end instruction switch 47 is a push button switch and operated when ending the preset procedural operation for the subject M. The X-ray fluoroscopic imaging becomes operable as to the next procedural operation and the end of the action once the operator pushes down the end instruction switch 47. In addition, according to the present Embodiment, the information of the rotation positions stored in correspondence with the respective memory switches 57 constituting the second memory switch group M2 is erased once the operator pushes down the end instruction switch 47.

In addition, the inventors set forth while limiting the four operation devices related to adjustment of the rotation position of the C-arm 9, but the device installed to the console 39 is not limited to such four devices. Specifically, an operation device as to the operation of the X-ray fluoroscopic imaging apparatus 1 such as a switch to turn on and off the main electric power, a switch to set up the imaging conditions, a switch to adjust the position of the table 3, or an emergency shutdown switch to stop can be arbitrary installed.

Figure 6:
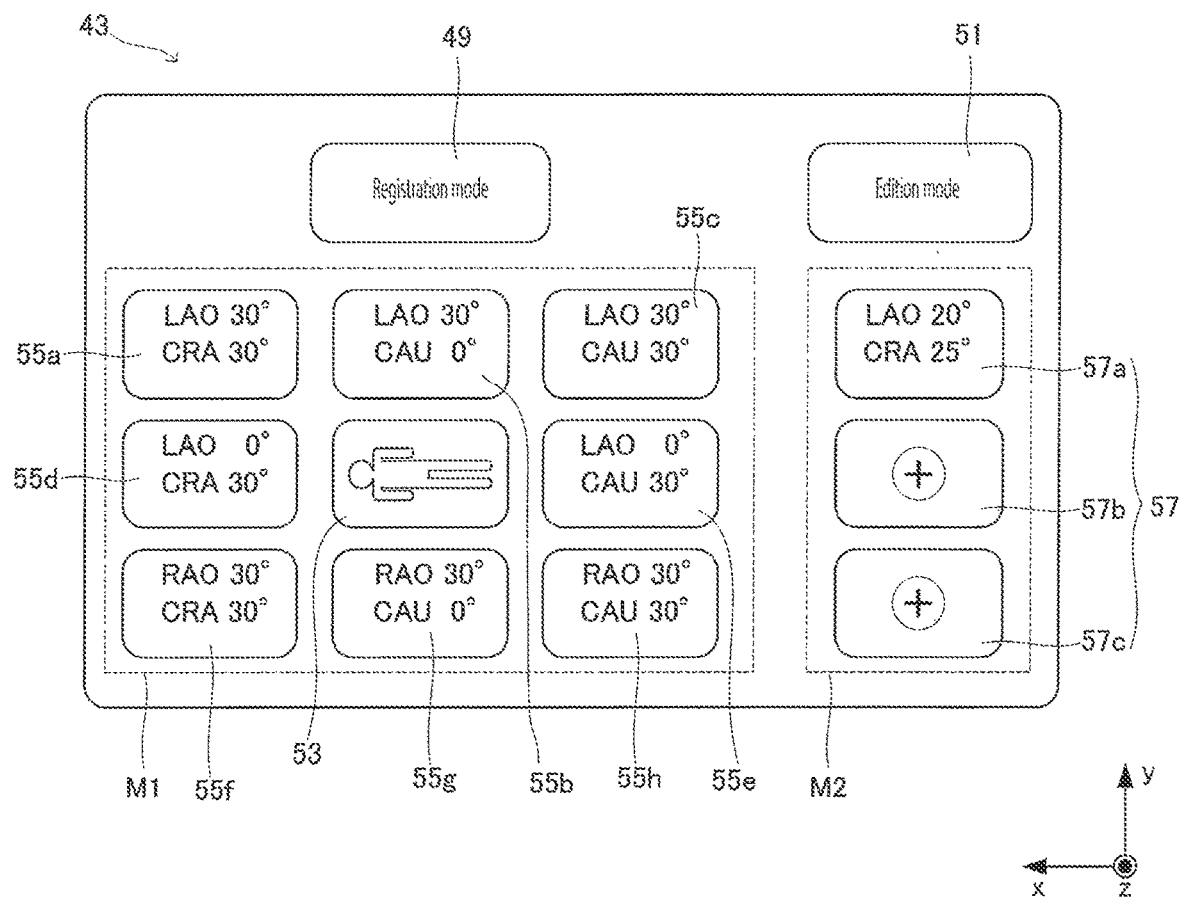
FIG. 6 is a view illustrating a display screen in the default mode of the touch panel according to the Embodiment.

Next, the inventors set forth the structure of the touch panel 43 in detail. FIG. 6 is a view illustrating the touch panel 43 in the default mode. The default mode is the mode of the touch panel 43 in the default (initial) state and the mode by which the auto-positioning operation to automatically rotate the C-arm 9 to the predetermined rotation position is executed.

<Structure of the Default Mode>

The touch panel 43 comprises a first memory switch group M1, a second memory switch group M2, a registration shifting switch 49, and an edition shifting switch 51. According to the present Embodiment, the respective switches are icons displayed on the touch panel 43.

The first memory switch group M1 comprises the center switch 53 and a plurality of memory switches 55. The center switch 53 is in place in the center of the first memory switch group M1 and displayed as a human shape symbol illustrating the subject M in the supine position. The respective memory switches 55 are in place around the center switch 53. According to the present Embodiment, referring to FIG. 6, it is given that the first memory switch group M1 comprises the eight memory switches 55a-55h. The number of the memory switches 55 is not limited eight and may be arbitrarily changed.

With regard to the first memory switch group M1, the respective memory switches are in correspondence with the information of a plurality of the rotation positions. According to the present Embodiment, the respective memory switches 55 are in correspondence with three kinds of the rotation position information. Specifically, referring to FIG. 7, the memory storage element 37 comprises a rotation position memory storage element 61. The rotation position memory storing element 61 stored the predetermined rotation position information in correspondence with the memory switches 55.

The rotation position memory storage element 61 comprises a plurality of the first memory 63, the second memory 64 and the third memory 65 in correspondence with the respective memory switches 55. Hereinafter, when the first memory 63, the second memory 64 and the third memory 65 are collectively called, it calls the memories 63-65. The respective memories 63-65 may store one kind of the rotation position information of the C-arm 9.

Figure 7:
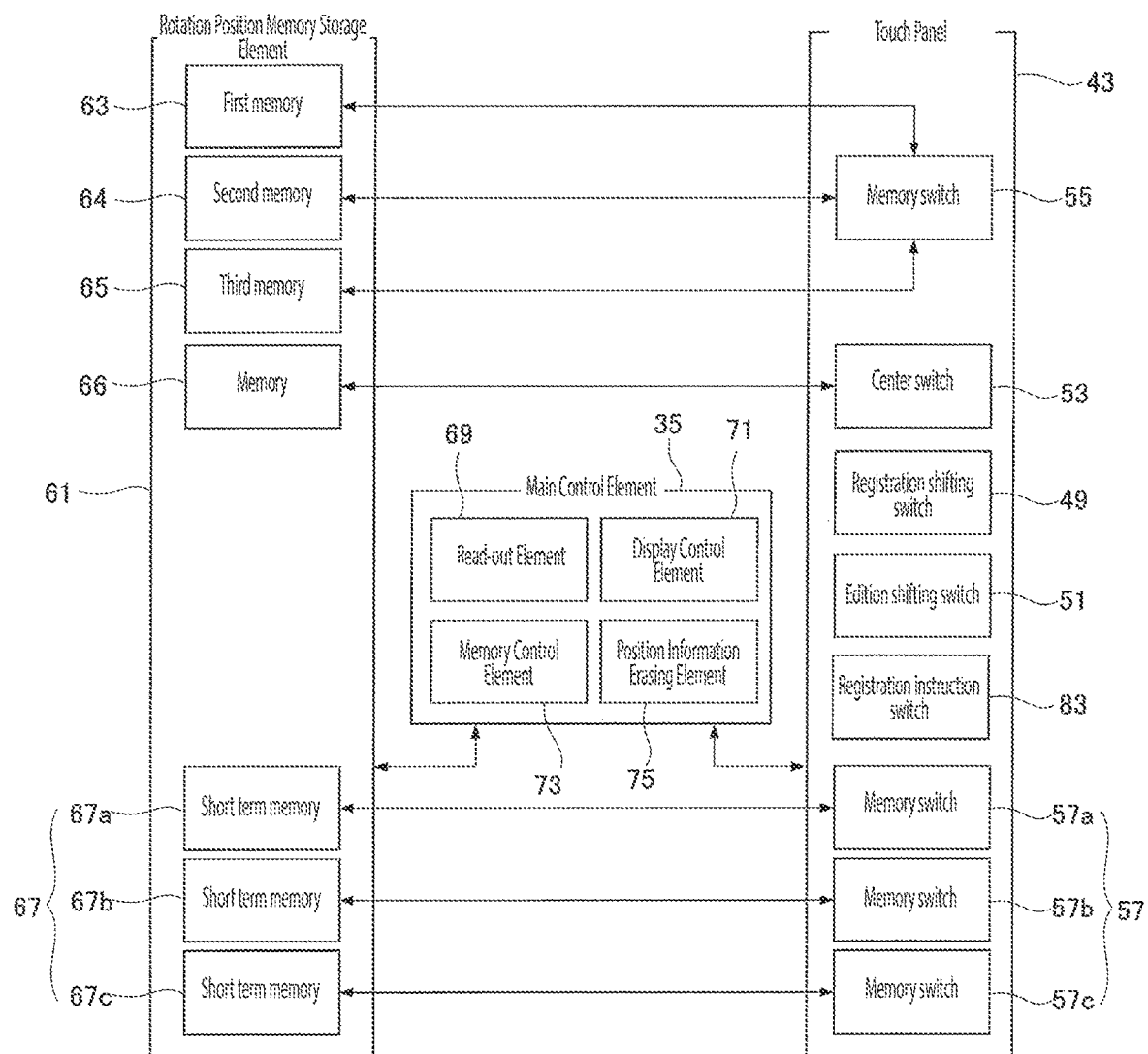
FIG. 7 is the functional block diagram illustrating the essential components of the X-ray fluoroscopic imaging apparatus according to the Embodiment.

Specifically, referring to FIG. 7, the respective memory switches 55 are in correspondence with total three memories 63-65. Therefore, the rotation position memory storing element 61 enables storing the respective memory switches 55 in correspondence with the three kinds of the rotation position information.

In addition, referring to FIG. 8, the memories 63-65 corresponding to the memory switches 55a have the sign a to make the memories 63a-65a to be distinguishable from other memories 63-65. Also, the memories 63-65 corresponding to the memory switches 55n have the sign n to be distinguishable from other memories 63-65.

The information of the rotation positions relative to the respective memory switches 55a-55h stored in advance in correspondence therewith is illustrated as shown in FIG. 8. Specifically, the memory switches 55a are stored in correspondence with the rotation position at which the C-arm 9 rotates in the CRA direction and the LAO direction from the default position shown in FIG. 1.

First, the information of the rotation position (rotation position information F1) at which the C-arm 9 rotates 30° in the LAO direction from the default position and then 30° in the CRA direction therefrom is preliminarily (in advance) stored in correspondence with the first memory 63a. The rotation position at which the C-arm 9 rotates 20° in the LAO direction from the default position and then 40° in the CRA direction therefrom is stored as the rotation position F2 in correspondence with the second memory 64a therein. The rotation position at which the C-arm 9 rotates 50° in the LAO direction from the default position and then 10° in the CRA direction therefrom is stored as the rotation position F3 in correspondence with the third memory 64a therein.

The information of the rotation positions F4-F6 as the information in correspondence with the memory switch 55b is stored respectively in the first memory 63 through the third memory 63b. The rotation positions F4-F6 are the positions following rotation of the C-arm 9 from the default position in the LAO direction. The information of the rotation positions F7-F9 as the information in correspondence with the memory switch 55c is stored respectively in the first memory 63c through the third memory 65c. The rotation position is where the C-arm 9 has rotated from the default position in the LAO direction and in the CAU direction.

Also, the information of the rotation positions F10-F21 is preliminarily stored as the information in correspondence with the memory switches 55d-55h. In addition, referring to FIG. 8, it is given that the rotation position information is not registered in the third memory 65g corresponding to the memory switch 55g and also the second memory 64h and the third memory 65h corresponding to the memory switch 55h respectively.

In addition, the rotation position memory storing element 61 further comprises the memory 66. The memory 66 is in correspondence with the center switch 53, and the information of the default position of the C-arm 9 is preliminarily stored as the rotation position F0 in the memory 66. Specifically, the center switch 53 is used when the C-arm 9 returns to the default position.

The position at which the respective memory switches 55 are in place on the basis of the center switch 53 is defined in accordance with the rotation position stored in correspondence with the memory switches 55. For example, the rotation position at which the C-arm 9 rotates from the default position in the CRA direction and in the LAO direction is stored in the memory switches 55a in correspondence therewith.

Referring to FIG. 4, the CRA direction is the left-side direction, and the LAO direction is the right-side direction on the basis of the position of the subject M. Therefore, the memory switch 55a in which the rotation position information in the CRA direction and in the LAO direction is in place upper left side on the basis of the center switch 53. Also, with regard to the memory switches 55b-55h, the position at which the memory switches 55b-55h are in place is decided corresponding to the direction of the rotation position stored in correspondence therewith. The position at which the center switch 53 is in place is the reference region of the present invention.

The second memory switch group M2 comprises a plurality of memory switches 57. According to the present Embodiment, referring to FIG. 6, it is given that the second memory switch group M2 comprises the three memory switches 57a-57c. The number of the memory switches 57 is not limited to three and may be arbitrarily changed. The first memory switch group M1 is used when the information of the rotation positions of the C-arm 9 is stored for a long time and on the other hand, the second memory switch group M2 is used when the information of the rotation positions of the C-arm 9 is stored temporarily.

Accordingly, the respective memory switches 57 are in correspondence with each one kind of the rotation position information. Specifically, the rotation position memory storing element 61 further comprises the same number of the short-term memories 67 as the number of the memory switches 57. According to the present Embodiment, the number of the memory switches 57 are three referring to FIG. 7, so that the rotation position memory storing element 61 comprises the three short-term memories 67a-67c. The short-term memory 67a is in correspondence with the memory switch 57a, and the short-term memory 67b is in correspondence with the memory switch 57b. The short-term memory 67c is in correspondence with the memory switch 57c.

Referring to FIG. 6 and FIG. 8, the rotation position at which the C-arm 9 rotates 40° from the default position in the LAO direction and also 30° in the CAU direction therefrom is preliminarily stored in the short-term memory 67a as the rotation position F22. It is given that the rotation position information is not registered yet in the short-term memory 67b and in the short-term memory 67c.

The registration shifting switch 49 is applied to input the instruction to shift the screen, which is displayed on the touch panel 43, from the default mode to the registration mode. Once the operator pushes down the registration shifting switch 49, the display screen of the touch panel 43 shifts from the default mode for performing the auto-positioning to the registration mode. The operation to instruct the first memory switch group M1 to store in correspondence with the predetermined rotation becomes workable by shifting to the registration mode.

The edition shifting switch 51 is applied to input the instruction to shift the screen, which is displayed on the touch panel 43, from the default mode to the edition mode. Once the operator pushes down the edition shifting switch 51, the display screen of the touch panel 43 shifts from the default mode for performing the auto-positioning to the edition mode. The operation to instruct the second memory switch group M2 to store in correspondence with the predetermined rotation position information can be available by shifting to the edition mode. The registration mode or the edition mode corresponds to the memory storing mode of the present invention. The registration shifting switch 49 or the edition shifting switch 51 corresponds to the memory storing shifting instruction element of the present invention.

Referring to FIG. 7, the main control element 35 further comprises a read-out element 69, a display control element 71, a memory storing control element 73 and a position information erasing element 75. The read-out element 69 selects and reads out the information of the rotation position stored in the memories 63-66 or the short-term memory 67 corresponding to the operation relative to such as the edition shifting switch 51 and the memory switches 55.

The display control element 71 displays the information of the rotation position that the read-out element 69 reads out, and the additional information as to such a read-out rotation position information on the touch panel 43. As an example of the additional information, such as the information of identifying the memory in which the read-out rotation position information is stored and the information of identifying whether the rotation position information stored in the memories 63-65 exists or not may be listed. The display control element 71 corresponds to the selection memory switch display mechanism of the present invention.

The memory control element 73 stores the rotation position information of the C-arm 9 in the rotation position memory storage element 61 due to the operation of the registration instruction switch 83 as a trigger later set forth. The position information erasing element 75 erases the rotation position information stored in correspondence with the respective memory switches 57 due to the predetermined operation relative to the X-ray fluoroscopic imaging apparatus 1 as a trigger. According to the present Embodiment, the push-down operation of the end instruction switch 51 is applied to the trigger for erasing the rotation position information. The position information erasing element 75 corresponds to the rotation position information erasing element of the present invention.

<Auto-Positioning Operation>

Figure 9A:
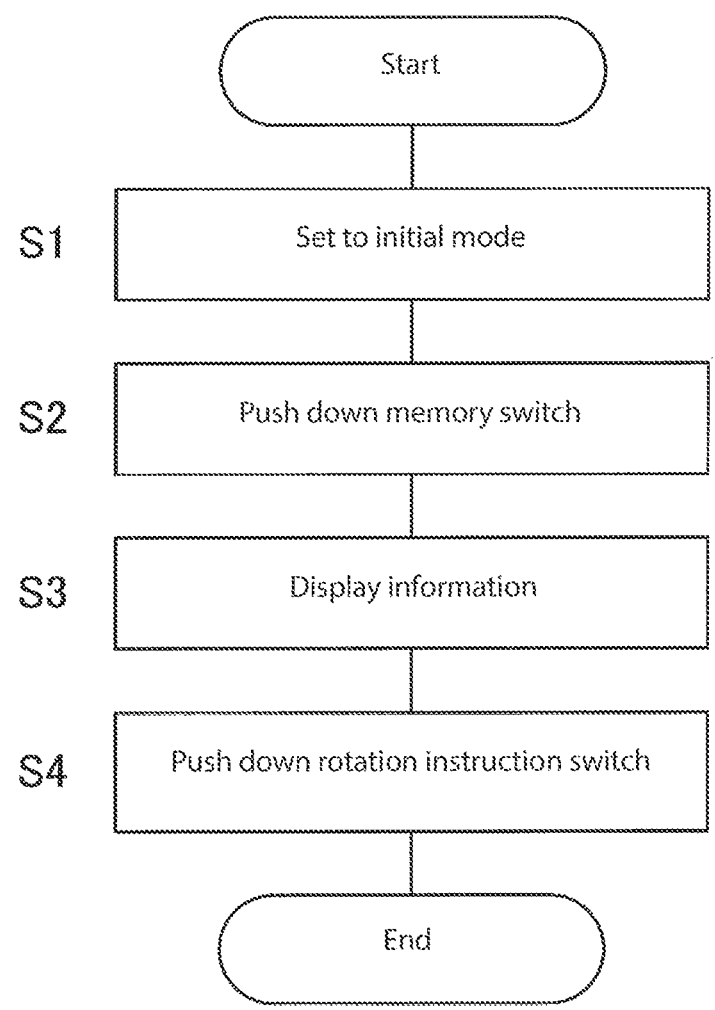
FIG. 9A, 9B, 9C are flow charts illustrating a variety of operation steps of the X-ray fluoroscopic imaging apparatus according to the aspect of the Embodiment.

Next, the inventor sets forth the action for the auto-positioning using the X-ray fluoroscopic imaging apparatus according to the present invention. FIG. 9A is the flow chart illustrating an auto-positioning operation. Here, the inventors set forth the case in which the C-arm 9 rotates automatically to the rotation position F8 that is the rotation position following the rotation 45° in the LAO direction from the default position and 20° in the CAU direction therefrom.

First, the operator set up the touch panel 43 of the console 39 to the default mode by executing the start-up thereof. Referring to FIG. 6, once the touch panel 43 shifts to the default mode, the display control element 71 displays the page (screen) for the auto-positioning on the touch panel 43.

Next, the operator selects the memory switches 55 or the memory switches 57 in correspondence with the information of the rotation position that is the target. When the memory switches 55 in correspondence with a plurality of the rotation position information is selected, the operator intuitively enables the proper selection of the memory switches 55 based on the position at which the memory switches 55*a*-55*h* are in place. As an example, when the C-arm 9 rotates from the default position in the LAO direction and in the CAU direction, the LAO direction is the upper side and the CAU direction is the right side from the reference that is a humanoid symbol displayed in the center switch 53. Specifically, for rotating in the LAO direction and the CAO direction, the operator can intuitively decide that it is adequate to select the memory switch 55*c* that is in place upper right side from the center switch as the reference.

In addition, the respective memory switches 57 are in correspondence with each one kind of the rotation position information, so that the display control element 71 can display such rotation position information on the touch panel in the default mode. Specifically, referring to FIG. 6, the information of the rotation position F22 in correspondence with the memory switch 57*a* and registered thereof is displayed. Accordingly, when the auto-positioning is executed using the rotation position information in correspondence with the memory switch 57, the operator can determine if the memory switch 57 in correspondence with the target rotation position exists or does not while watching the screen of the touch panel 43 in the default mode. Here, referring to FIG. 6, it can be determined by visually recognizing the display of the second memory switch group M2 that the respective memory switches 57*a*-57*c* are not in correspondence with the information of the rotation position F8. Therefore, the operator selects the memory switch 55*c* but not the memory switch 57.

When selecting the memory switches 55, the operator can read out the target rotation position information from the memories 63-65 by operating the selected memory switches 55 in the respectively different manners (Step S3). According to the present Embodiment, the memories 63-65 that are read-out targets are distinguished due to the number of pushing-downs of the memory switches 55.

Specifically, the read-out element 69 reads out the rotation position information stored in the first memory 63 by operating the memory switches 55 in the manner (first manner) in which the memory switches 55 is pushed down once by the operator. The read-out element 69 reads out the rotation position information stored in the second memory 64 by the operation (second manner) in which the memory switches 55 are pushed down twice. The read-out element 69 reads out the rotation position information stored in the third memory 65 by operation (third manner) in which the memory switches 55 are pushed down three times. In addition, when the memory switches 55 are pushed down four times, the target read out by the read-out element 69 returns to be the first memory 63 and further, every time when the memory switch 55 is pushed down, the memory that is the target to be read out is changed.

Figure 11:
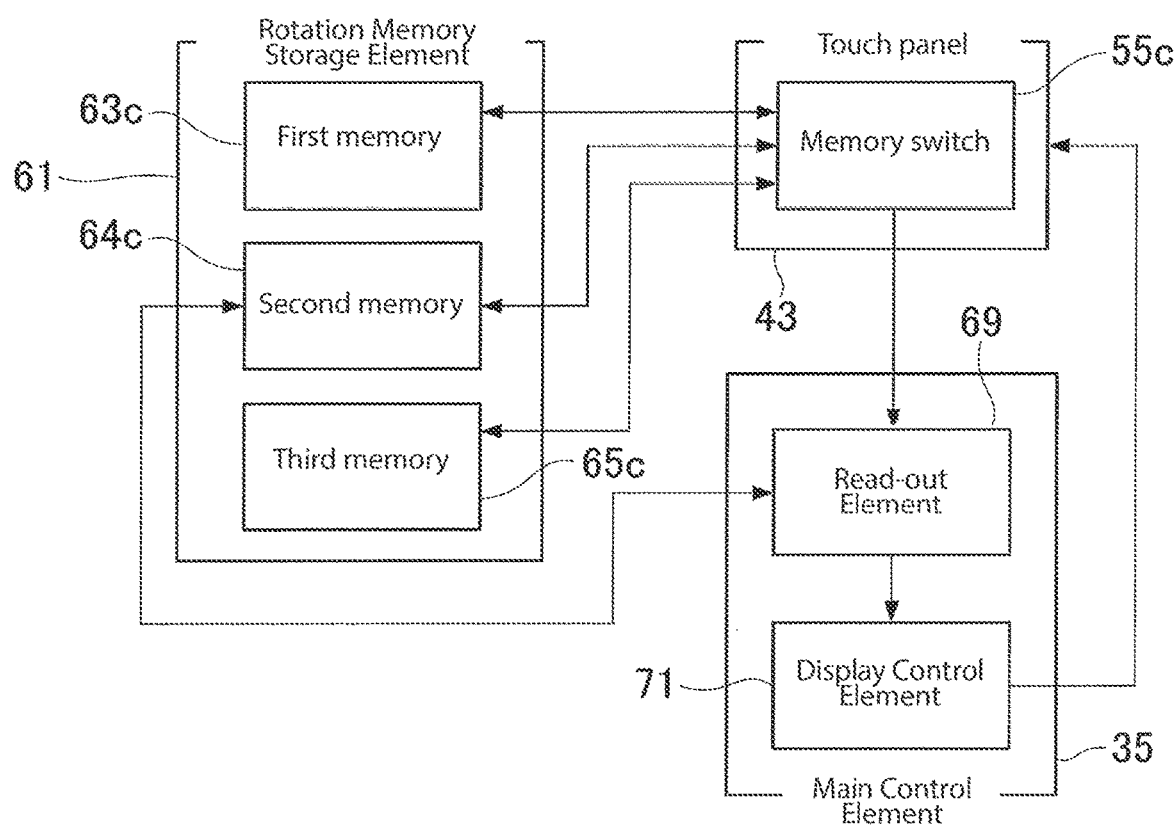
FIG. 11 is a schematic diagram illustrating the essential component of the X-ray fluoroscopic imaging apparatus at Step S3 according to the aspect of the Embodiment.

Referring to FIG. 8, the information of the rotation position F8 is stored in the second memory 64*c* in correspondence with the memory switch 55*c*. Therefore, the operator enable the selection of the information of the rotation position E8 by pushing down the memory switch 55*c* twice. Once the operation of pushing down the memory switch 55*c* twice is executed as the trigger, the read-out element 69 determines that the read-out target is the second memory 64*c*. And referring to FIG. 11, the rotation position information is read out from the second memory 64*c* and the information of such the information of such a rotation position F8 is sent out to the display control element 71.

The display control element 71 displays the read-out rotation position information F8 on the touch panel 43. At this time, the display control element 71 displays not only the information of the rotation position F8 but also the information (additional information Sp) denoting that the latest operated memory switch is the memory switch 55*c* of the memory switches 55 and the information (additional information Qt) denoting that the target for the read-out processing done by the read-out element 69 is the second memory 64 between the first memory 63 and the third memory 65 on the touch panel 43. The display screen of the touch panel 43 changes from the state referring to FIG. 6 to the state referring to FIG. 10 due to the control that the display control element 71 executes. In addition, according to the present invention, the latest operated memory switches 55 means the memory switches 55 is subject to the latest operation selected as the target for the auto-positioning operation, i.e., the memory switches 55 that is the selection target for the auto-positioning operation at the present time.

Figure 10:
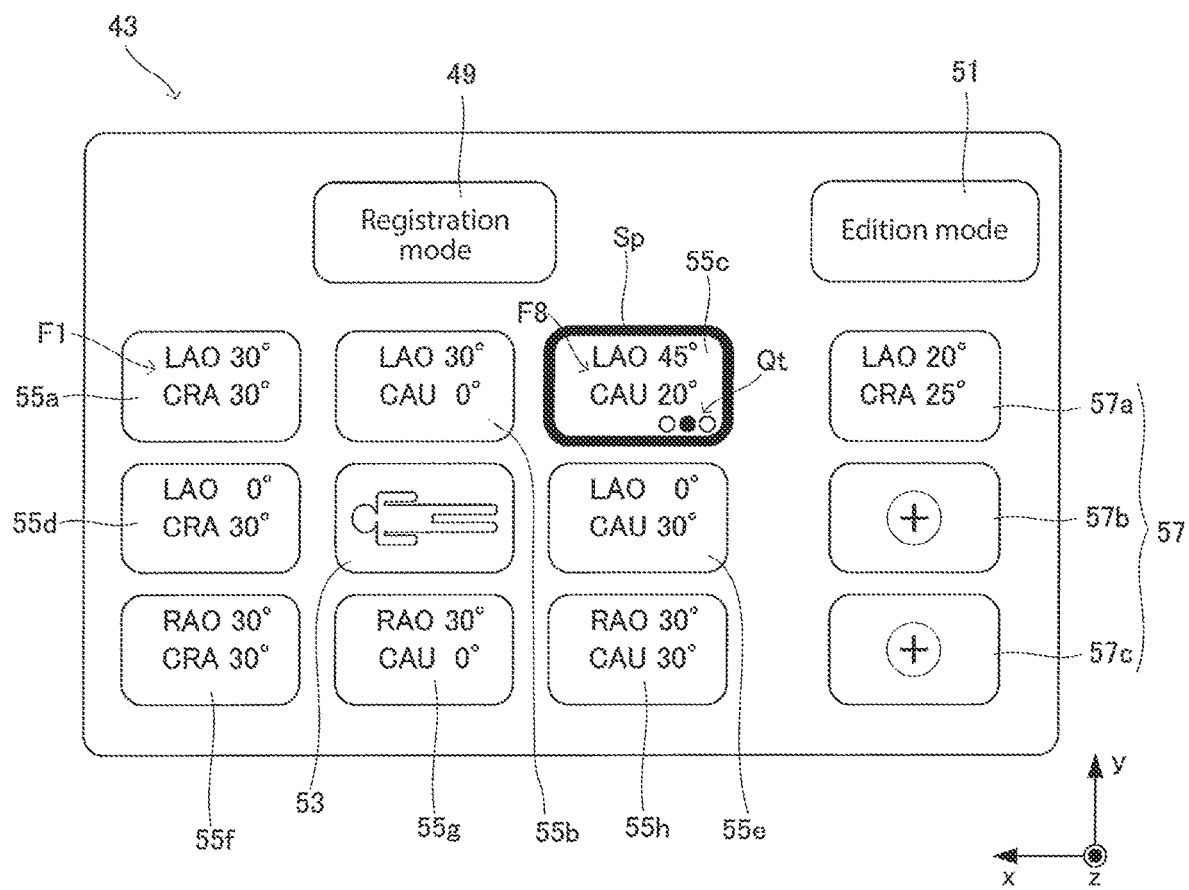
FIG. 10 is a view illustrating a touch panel display screen at Step S3 according to the Embodiment.

As the example of the additional information Sp, the selected memory switches 55 turns a light on, blink the light and change the color and so forth. Referring to FIG. 10, according to the present Embodiment, the memory switches 55 selected at the present time is provided with a thick line frame which indicates that is the additional information Sp. The additional information Sp is displayed on the touch panel 43, so that the operator can intuitively understand that the memory switch 55c is selected from the first memory switch group M1.

According to the present Embodiment, the additional information Qt includes two kinds of information that is the information identifying the number of the rotation positions registered in the memory switches 55 and the information identifying the memories 63-65 that are the current read-out targets. Referring to FIG. 10, the additional information Qt are represented by the three circular symbols arrayed in series from right to left. The number of the circular symbols denotes the number of the rotation positions registered in such memory switches 55. The additional information Qt added to the memory switches 55 has three symbols. Consequently, the operator can confirm by visually recognizing the additional information Qt that the number of the rotation position information already registered in the memory switches 55 at the present time is three.

In addition, the location of the black circular symbol in the series of the three circular symbols forming the additional information Qt identifies which one is the current read-out target among the memories 63-65. For an example, provided the read-out target is the first memory 63, the additional information Qt appears as ●○○. Specifically, the left end symbol is displayed as the black circle and the rest of two symbols are displayed as the white circle. Provide the read-out target is the second memory 64, the additional information Qt appears as ○●○. Specifically, the second symbol from left is displayed as the black circle. Provided the read-out target is the second memory 64, the additional information Qt appears as ○○●. Specifically, the third symbol from left is displayed as the black circle.

When the read-out and displayed rotation position in the memory switches 55 coincides with the rotation position of the C-arm 9 at the present time, the display control element 71 displays the additional information in the memory switches 55. The additional information is displayed in the different manner from the additional information Sp and a whole or a part of the memory switches 55 that are the current selection targets may be blinked or subject to change the color thereof. The operator can confirm by visually recognizing the additional information that the C-arm 9 has reached to the rotation position displayed in the selected target memory switches 55. According to the present Embodiment, the additional information is deemed displayed by blinking and displaying the whole of the memory switches 55 selected at the present time.

The operator visually recognizes the rotation position information and the additional information Qt displayed in the memory switches 55 every time when the memory switches 55 are pushed down. The operator identifies the read-out target memories 63-65 and confirms the contents of the read-out rotation position information by visually recognizing the rotation position information and the additional information Qt.

Referring to FIG. 10, the additional information Qt appeared as ○●○ is displayed in the memory switches 55 by executing the operation in which the memory switch 55c is pushed down twice. Therefore, the operator can intuitively understand by visually recognizing such an additional information Qt that the information of the rotation position information F8 is read out in the second memory 64c among the first memory 63c, the second memory 64c and the third memory 65c.

The operator pushes down the rotation instruction switch 49 to rotate the C-arm to the target position following confirming that the read-out and displayed rotation position information in the touch panel 43 is the information of the target rotation position F8 (Step S4). Specifically, once pushing down the rotation instruction switch 49 in the state in which the information of the rotation position F8, the additional information Sp and the additional information Qt are displayed in the memory switches 55, the C-arm 9 is subject to an action to rotate to the rotation position F8 while pushing down the rotation instruction switch 49. The C-arm 9 rotates and once reached to the rotation position F8 that is the target rotation position, the additional information indicating that the current position of the C-arm 9 coincides with the rotation position F8 are displayed in the memory switches 55. The operator visually recognizes such an additional information and confirms that the C-arm 9 has rotated to the target rotation position F8 thereby. The operator performs the X-ray fluoroscopy or the X-ray imaging by irradiating the X-ray to the subject M from the X-ray tube 5 following confirming that the C-arm 9 has rotated to the target rotation position.

<Structure of the Registration Mode>

In addition, according to the present Embodiment, the number of the circular symbols forming the additional information Qt is three. Consequently, when the information of the target rotation position is not displayed on the touch panel 43 even though the operator pushes down the memory switches 55 three times, the operator can understand easily and quickly that no target rotation position information is stored in memory switches 55.

As an example, in the case of using the registration mode, the case in which the information of the target rotation position is not stored in none of the memory switches 55 may be listed. In such a case, the operator shifts the touch panel 43 to the registration mode and executes the operation to store the new target rotation position. Here, the inventors set forth the configuration in which the new rotation position information in correspondence with the memory switches 55 is applied to overwrite and stored in the registration mode.

When overwritten with the new rotation position information in correspondence with the memory switches 55, first the registration shifting switch 49 is pushed down to shift the touch panel 43 from the default mode to the registration mode. The display control element 71 changes the display screen of the touch panel 43 from the state referring to FIG. 6 to the state referring to FIG. 12 due to shifting to the registration mode.

Figure 12:
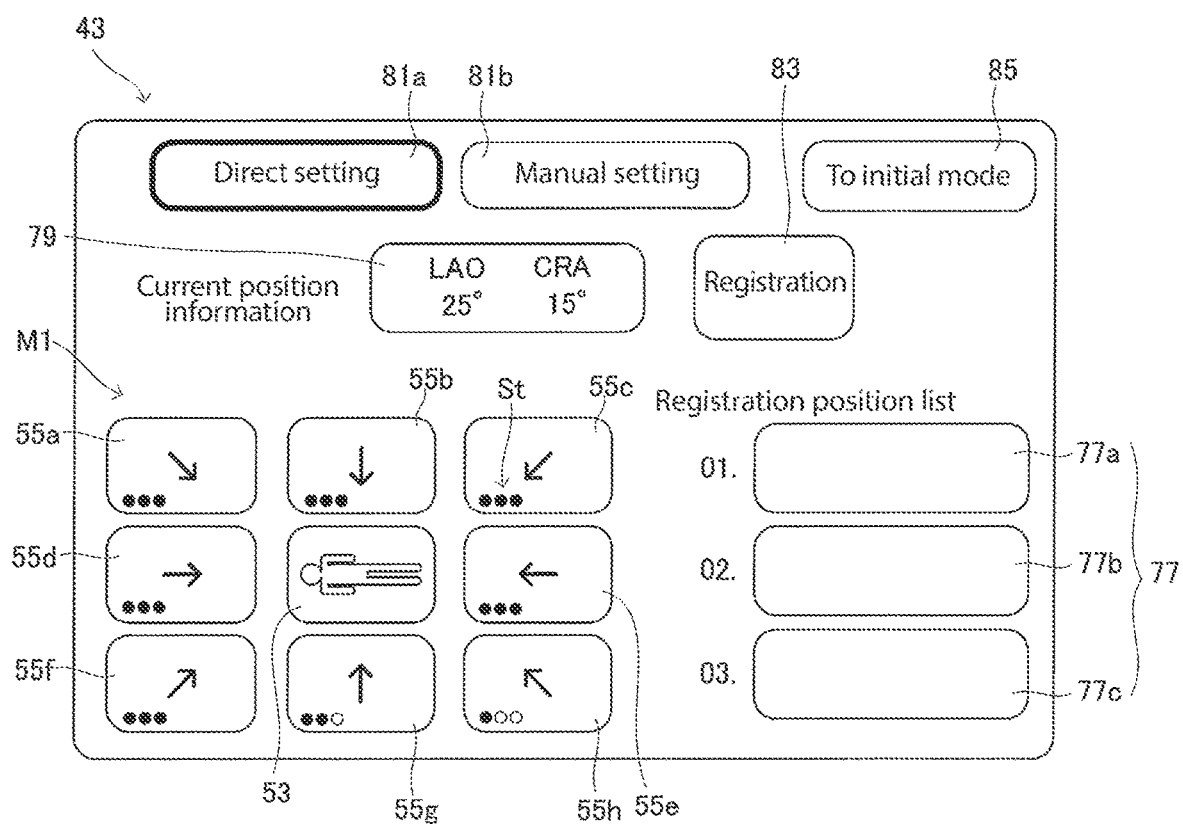
FIG. 12 is a view illustrating a touch panel display screen at Step P1 according to the Embodiment.

Referring to FIG. 12, the touch panel 43 that shifts to the registration mode comprises a first memory switch group M1, a memory selection switch 77, a current position display element 79, a registration setting selection switch 81, a registration instruction switch 83 and a mode return switch 85. The display control element 71 shifts to the registration mode and thereby displays the additional information St that indicates if the stored rotation position information exists or not as to the respective memory switches 55 in correspondence with a plurality of the memories 63-65 of the first memory switch group M1.

The additional information St is represented by the three circular symbols arrayed in series from right to left as well as the additional information Qt. The left end symbol indicates if the rotation position information exists or not in the first memory 63. The center symbol indicates if the rotation position information exists or not in the second memory 64. The right end symbol indicates if the rotation position information exists or not in the second memory 65. When the symbol is the black circle, it is indicated that the rotation position information is already registered in the memories 63-65 corresponding to such a symbol. When the symbol is the white circle, it is indicated that no rotation position information is yet registered in the memories 63-65 corresponding to such a symbol.

As an example, referring to FIG. 8, the rotation position information is already registered respectively in every memory from the first memory 63 through the third memory 65 respectively in correspondence with the memory switches 55a-55f. Consequently, all three kinds of additional information St displayed in the memory switches 55a-55f are indicated by the black circular symbols (●●●). With regard to the memory switch 55g, the rotation position information is not yet registered only in the third memory 65g. Consequently, the additional information St displayed in the memory switch 55g is indicated by having the three circular symbols (●●○) having the white circle at the right end location. With regard to the memory switch 55h, the rotation position information is registered only in the first memory 65h. Consequently, the additional information St displayed in the memory switch 55h is indicated by having the three circular symbols (●○○) having the black circle only at the left end location.

The operator visually recognizes the additional information St and thereby can intuitively and comprehensively understand if the stored rotation position information exists or not as to the respective memories 63-65 corresponding to the memory switches 55a-55h.

The memory selection switches 77 selects the memories 63-65 that are the targets in which the rotation position information is newly stored. The memory selection switches 77 comprises the memory selection switch 77a corresponding to the first memory 63, the memory selection switch 77b corresponding to the second memory 64 and the memory selection switch 77c corresponding to the third memory 65. The number of the memory selection switches 77 is determined corresponding to the number of rotation position information that is stored in accordance with the memory switches 55.

The current position information display element 79 displays the information of the rotation position of the C-arm 9 at the present time that the rotation position detection element 33 detects. The registration setting selection switch 81 comprises a first switch 81a that shifts the information of the rotation position of the C-arm 9 at the present time to the state to be registered (direct registration mode) and the second switch 81b that shifts the information of the rotation position that the operator sets arbitrary to the state to be registered (manual registration mode). The state of the registration mode in the initial state is the state in which the first switch 81a selects the direction registration mode.

<Operation of the Registration Mode>

Figure 9B:
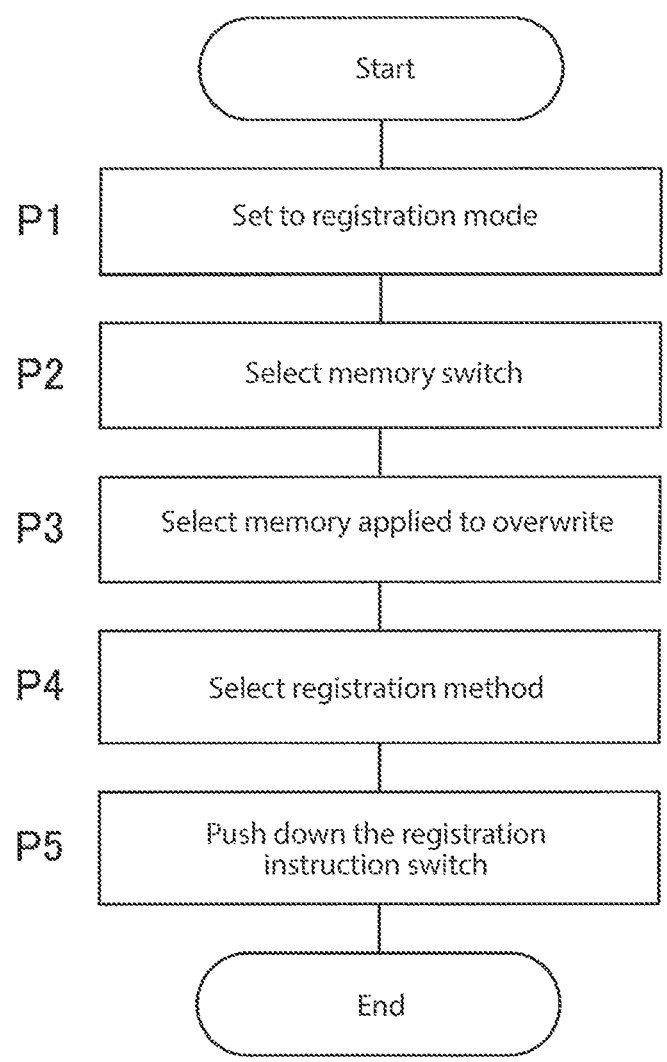

Here, the inventors set forth the operation to register the new rotation position information with the memory switches 55 in the registration mode. FIG. 9B is the flow chart illustrating the operation to register the new rotation position information in the memory switches 55. Here, the inventors set forth the case in which the information of the rotation position FA that is the current position of the C-arm 9 is newly registered relative to the third memory 65a corresponding to the memory switch 55a. The rotation position FA is the position to which the C-arm 9 rotates 25° in the LAO direction from the default position and 15° in the CRA direction therefrom.

First, once the operator pushes down the registration shifting switch 49, the touch panel 43 shifts from the default mode to the registration mode (Step P1). Referring to FIG. 12, once the touch panel 43 shifts to the registration mode, the display control element 71 displays the screen for the registration mode on the touch panel 43.

Figure 13:
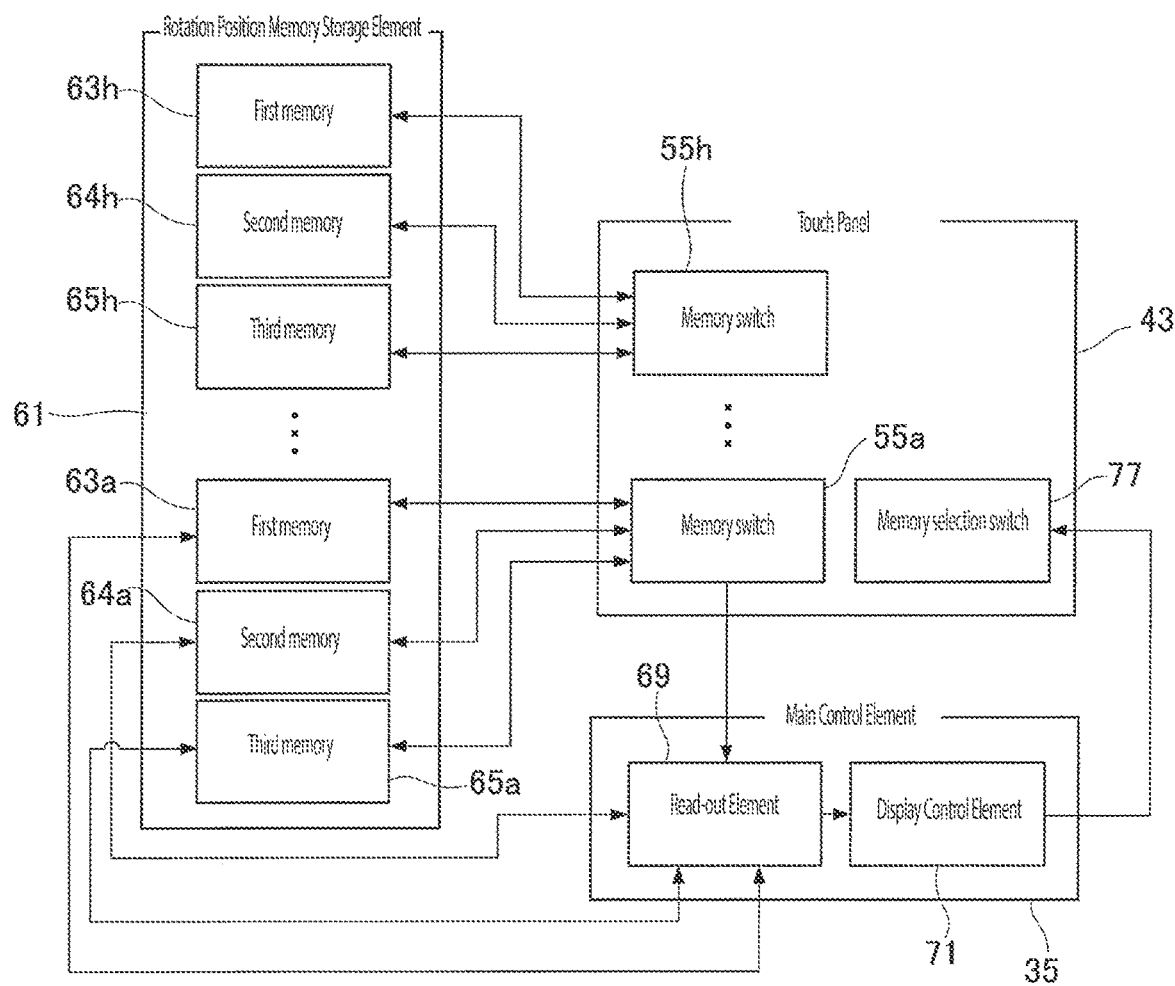
FIG. 13 is a schematic diagram illustrating the essential component of the X-ray fluoroscopic imaging apparatus at Step P2 according to the aspect of the Embodiment.

Next, the operator selects the memory switches 55 that is the target in which the new rotation position information is registered (Step P2). Here, the registration target is the memory switch 55a, so that the operator pushes down the memory switch 55a. As the trigger that is the action of selecting and pushing down the memory switches 55 and pushing down, the display control element 71 displays the additional information for identifying the selected memory switches 55 on the touch panel 43. Referring to FIG. 13, according to the present Embodiment, the frame of the selected memory switch 55 (here, memory switch 55a) is displayed by the thick line to indicate corresponding to such an additional information.

Figure 14:
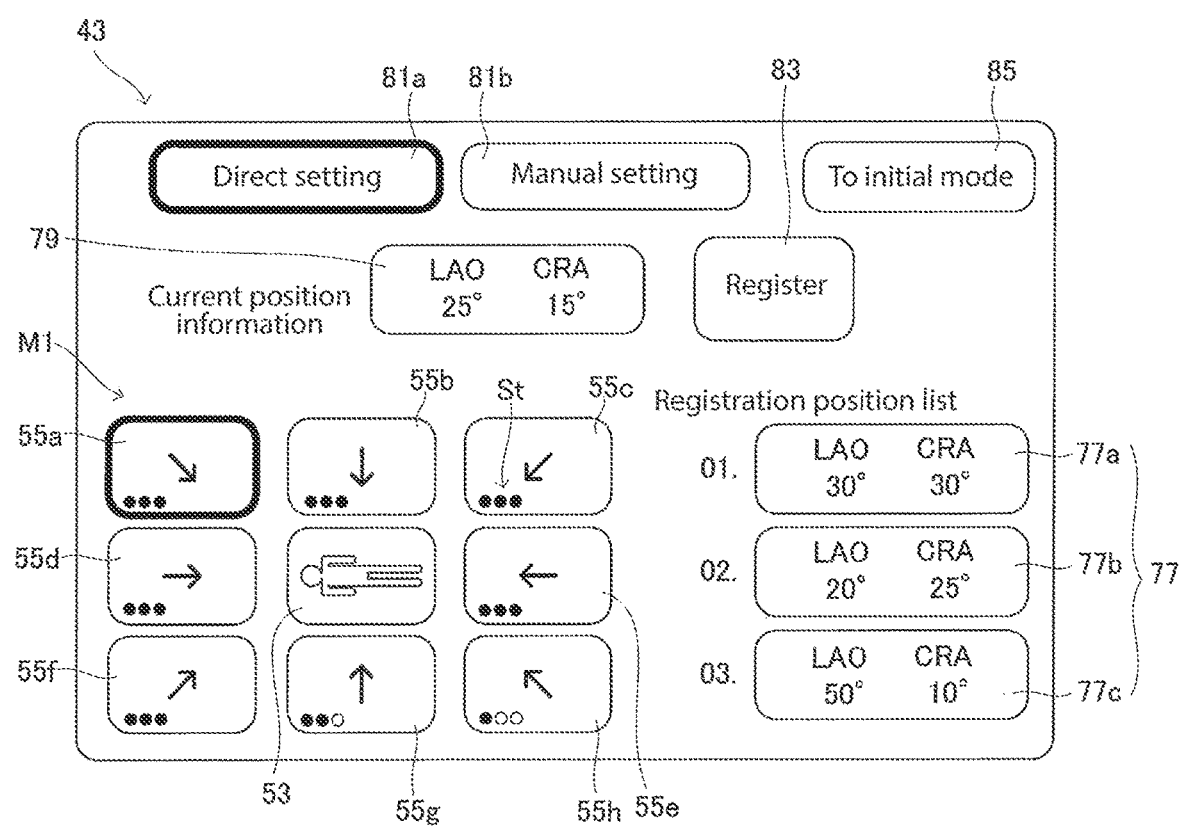
FIG. 14 is a view illustrating a touch panel display screen at Step P2 according to the Embodiment.

In addition, referring to FIG. 13, once the memory switches 55 is selected to be the register target, the read-out element 69 reads out the rotation position information that is stored in the respective memories 63-65 in correspondence with the selected memory switch 55 and sends such information to the display control element 71. The display control element 71 displays the respective read-out rotation position information in the memory selection switch 77. As a result, referring to FIG. 14, the information of the rotation position F1 is displayed in the memory selection switch 77a. As well, the information of the rotation positions F2 and F3 is displayed in the memory selection switch 77b and 77c.

Figure 15:
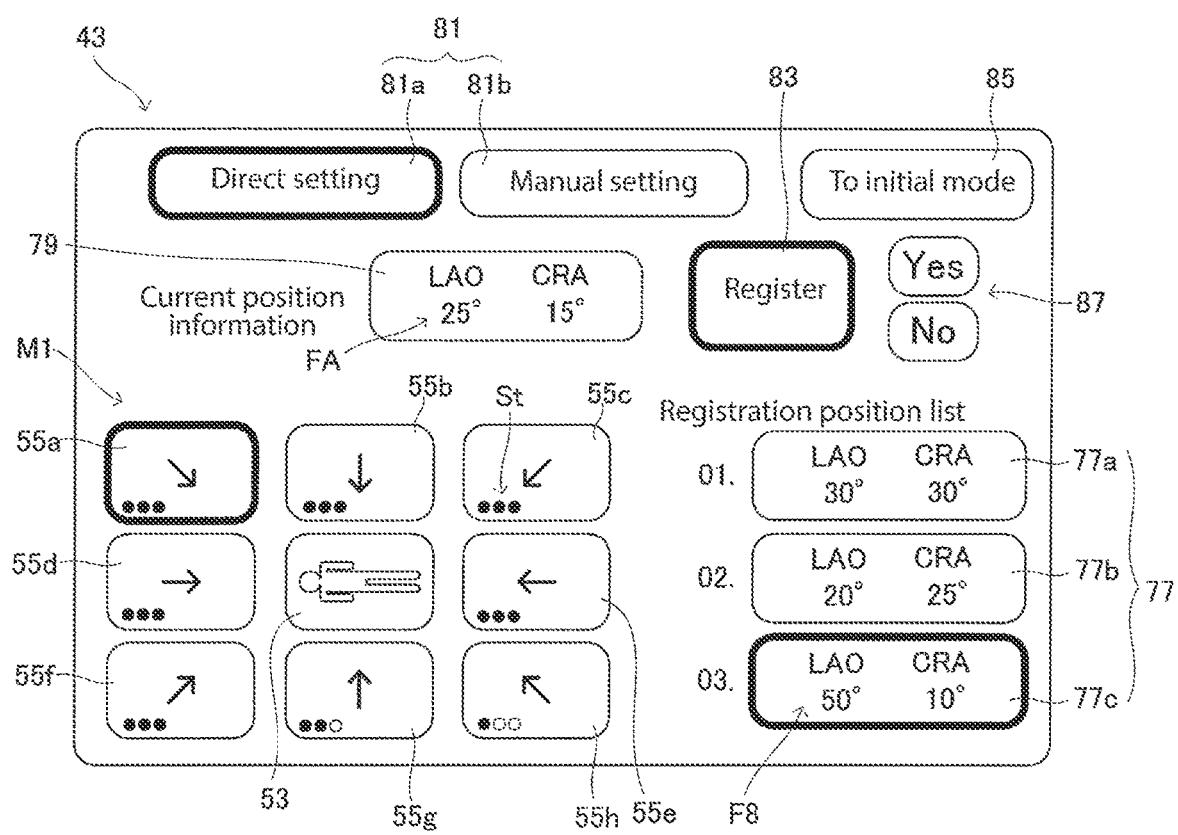
FIG. 15 is a view illustrating a touch panel display screen at Step P5 according to the Embodiment.

Once the memory switch 55 is selected, the operator confirms the rotation position information displayed in the respective memory selection switches 77 and selects the target memory to be overwritten (Step P3). The target memory to be overwritten and registered is the third memory 65a, so that the memory selection switch 77 corresponding to the third memory 65a is selected and pushed down. Referring to FIG. 15, as the trigger that is the selection of the memory selection switch 77, the display control element 71 displays the additional information for implying the selection target relative to the selected memory selection switch 77. Referring to FIG. 15, the frame of the memory selection switch 77c is denoted by the thick line, so that the additional information can be pointed as well as the additional information Sp.

Once the memory selection switch 77 is selected, the operator selects either the direct registration mode or the manual registration mode using the registration setting selection switch 81 (Step P4). Now, the direct registration mode to register the rotation position of the C-arm 9 at the present time is already selected at the present time, the operator pushes down the registration instruction switch 83 without operating the registration setting selection switch 81 (Step P5).

Figure 16:
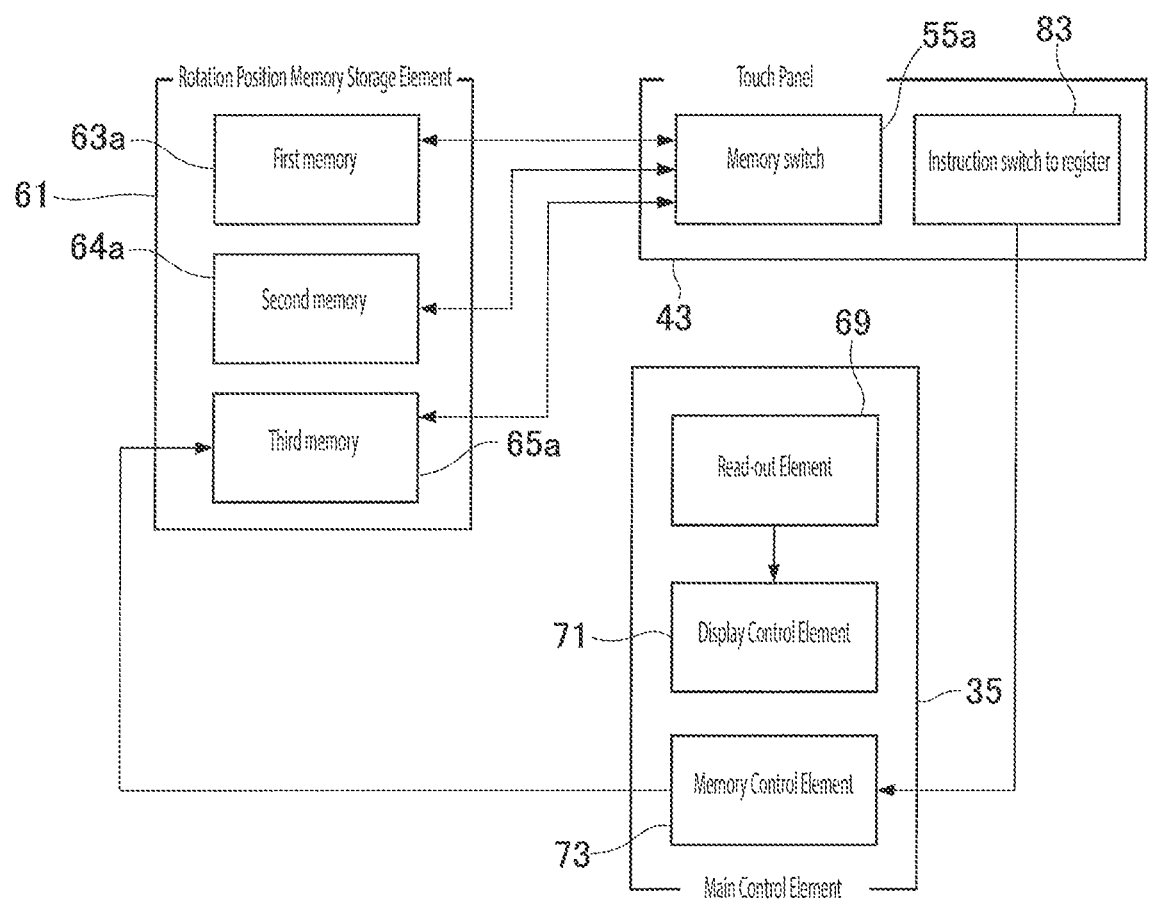
FIG. 16 is a functional block diagram illustrating the essential component of the X-ray fluoroscopic imaging apparatus at Step P5 according to the Embodiment.

Referring to FIG. 15, once the registration instruction switch 83 is pushed down, the information of indicating that such a pushing-down has been executed is displayed in the registration instruction switch 83 by the display control element 71 and also the confirmation key 87 is displayed thereby. Referring to FIG. 16, the operator operates the key for carrying on the registration (here, the key displayed as Yes) among the confirmation keys 87, so that the memory control element 73 overwrites the information of the rotation position and stores therein relative to the third memory 65a in which the information of the rotation position F3 is stored. When the touch panel 43 is returned to the default mode, the touch panel 43 shifts from the registration mode to the default mode along with pushing down the mode return switch 85.

The rotation position of the C-arm 9 at the present time can be registered in corresponding with the memory switches 55 in the direct registration mode. Specifically, the information of the rotation position can be quickly registered while skipping the operation to confirm the accurate rotation position of the C-arm 9 at the present time.

Figure 17:
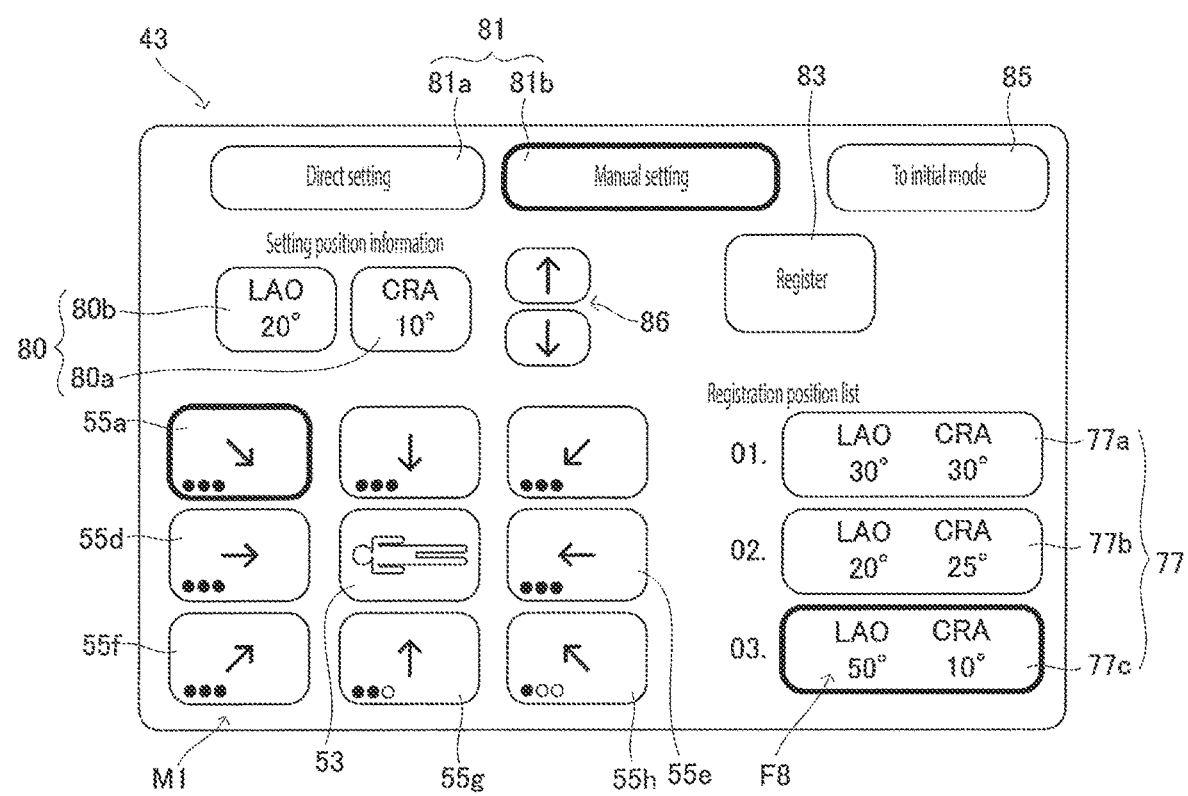
FIG. 17 is a view illustrating a touch panel at Step P4 when the manual selection mode is selected according to the Embodiment

The second switch 81b is pushed down at Step P4 when the rotation position information is registered due to the manual registration mode. The display screen of the touch panel 43 is switched to the screen shown in FIG. 17 by pushing down the second switch 81b. Specifically, the setting position display element 80 and the adjustment key 86 are displayed on the touch panel 43 instead of the current position display element 79. The operator operates arbitrarily such as the adjustment key 86 to adjusts so that the rotation position information to be displayed in the setting position display element 80 is the rotation position FA.

As a specific example of the adjustment operation, the angle of the body axis direction (CRA/CAU) becomes adjustable by pushing down the body axis direction adjustment element 80a that is place in the right side of the setting position display element 80. The degree of the angle in the body axis direction can be arbitrarily adjusted by arbitrarily operating the upward direction key or the downward direction key consisting of the adjustment keys 86 following pushing down the body axis direction adjustment element 80a. In addition, the angle of the body axis circumference direction (LAO/RAO) becomes adjustable by pushing down the body axis circumference direction adjustment element 80b that is place in the left side of the setting position display element 80.

The operation of Step P5 is executed following adjusting for displaying the information of the rotation position FA in the setting position display element 80. Specifically, the operator pushes down the registration instruction switch 83 and the confirmation key 87. The memory control element 73 overwrites the information of the rotation position FA displayed in the setting position display element 80 on the third memory 65a and stores thereon by operating the key for carrying on the registration among the confirmation keys 87.

The C-arm 9 is not needed to be shifted to the actual target rotation position due to the manual registration mode. Consequently, when the information of the rotation position to be preregistered is known, the information of the rotation position can be further quickly registered in correspondence with the memory switches 55.

<Structure of the Editing Mode>

When the procedural operation proceeds for the subject M, the action to acquire the X-ray images of the same region of interest from a plurality of different directions may be repeated. For example, the back-and-forth operation for the C-arm 9 is repeatedly progressed between the first rotation position Fp and the second rotation position Fs, which are defined based on the subject M or a kind of procedural operation.

When the back-and-forth operation is performed on the C-arm 9 between predetermined rotation positions, it is preferable that the auto-positioning operation is executed to cut the time needed for back-and-forth operation while temporally registering the information of the rotation position Fp and the information of the rotation position Fs. It is common that the first rotation position Fp and the second rotation position Fs are determined as the rotation positions at which the desired X-ray fluoroscopic images can be obtained by performing the X-ray fluoroscopy while shifting the C-arm 9 to a variety of rotation positions relative to the region of interest.

When the registration of the rotation position is needed in the short-term during proceeding the procedural operation, the operator switches the touch panel 43 to the edition mode and registers the information of the rotation position Fp and the rotation position Fs in correspondence with the second memory switch group M2. Now, the inventors set forth the configuration wherein the new rotation position information is temporarily stored in correspondence with the memory switch 57 in the edition mode.

When overwritten with the new rotation position information in correspondence with the memory switches 57, first the edition shifting switch 51 is pushed down to shift the touch panel 43 from the default mode to the edition mode. The display control element 71 changes the display screen of the touch panel 43 from the state referring to FIG. 6 to the state referring to FIG. 18 by shifting to the edition mode.

The touch panel 43 that shifts to the edition mode comprises a first memory switch group M2, a plurality of memory switches 57a-57c constituting the second memory switch group M2, a current position display element 89 and a mode return switch 91.

The read-out element 69 reads out the rotation position information that is stored in the short-term memories 67a-67c in correspondence with the memory switches 57a-57c by shifting to the edition mode. The display control element 71 displays the rotation position information read out from the short-term memories 67a-67c in the respective memory switches 57a-57c in correspondence therewith. Specifically, the information of the rotation position F21 is displayed in the memory switch 57a.

When the information of the rotation position is not stored in the corresponding short-term memory 67, the display control element 71 displays the additional information Rp indicating that the rotation position information is not registered in the appropriate memory switch 57. According to the present Embodiment, the figure (circle plus sign) combining a plus sign (+) and a circle surrounding such a plus sign is applied to the additional information Rp.

Referring to FIG. 8, the rotation position information is not registered yet in the short-term memory 67b and in the short-term memory 67c. Consequently, the display control element 71 displays the additional information Rp in the memory switch 57h and the memory switch 57c. The operator visually recognizes the information displayed in the memory switches 57a-57c and thereby can intuitively understand if the rotation position information exists or not.

Figure 18:
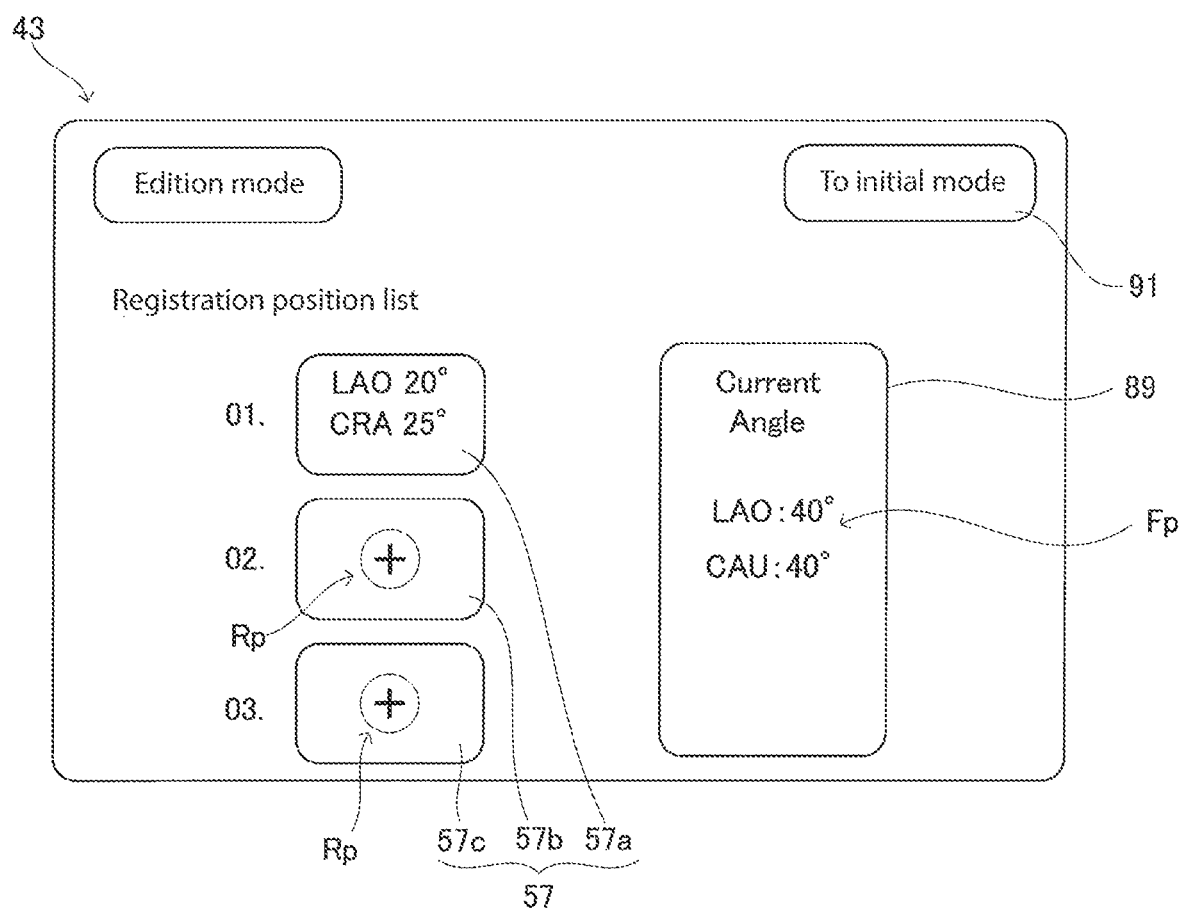
FIG. 18 is a view illustrating a touch panel display screen at Step T1 according to the Embodiment.

The current position information display element 89 displays the information of the rotation position of the C-arm 9 at the present time that the rotation position detection element 33 detects. Referring to FIG. 18, the current position display element 89 displays the first rotation position Fp (LAO) 40°, CAU 40°). The mode return switch 91 is the switch through which an instruction for the touch panel 43 to return from the edition mode to the default mode is input.

<Operation of the Edition Mode>

Figure 9C:
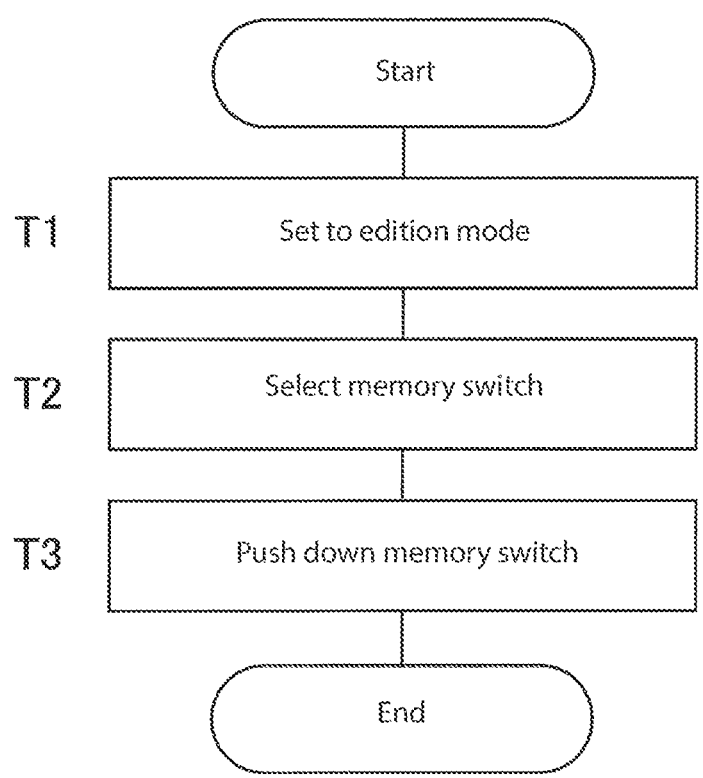

Here, the inventors set forth the operation to register the new rotation position information with the memory switches 57 in the edition mode. FIG. 9C is the flow chart illustrating the operation to register the new rotation position information in the memory switches 57. Here, the inventors set forth the case in which the information of the rotation position Fp and the information of the rotation position Fs (RAO40°, CAU40°) are temporarily registered relative to the memory switches 57. According to the present Embodiment, no rotation position information in the memory switch 57b and 57c is registered, the information of the rotation position Fp is deemed to register in correspondence with the memory switch 57c and the information of the rotation position Fp is deemed to register in correspondence with the memory switch 57c.

First, the operator pushes down the edition shifting switch 51 to shift the display screen of the touch panel 43 shifts from the default mode to the edition mode (Step T1). Referring to such a FIG. 18, once the touch panel 43 shifts to the registration mode, the display control element 71 displays the screen for the edition mode on the touch panel 43.

Next, the operator selects the memory switches 57 that are the targets in which the new rotation position information is registered (Step T2). The target to register the rotation position Fp displayed in the current position display element 89 is the short-term memory 67b corresponding to the memory switch 57b, so that the operator selects the memory switch 57b.

Figure 19:
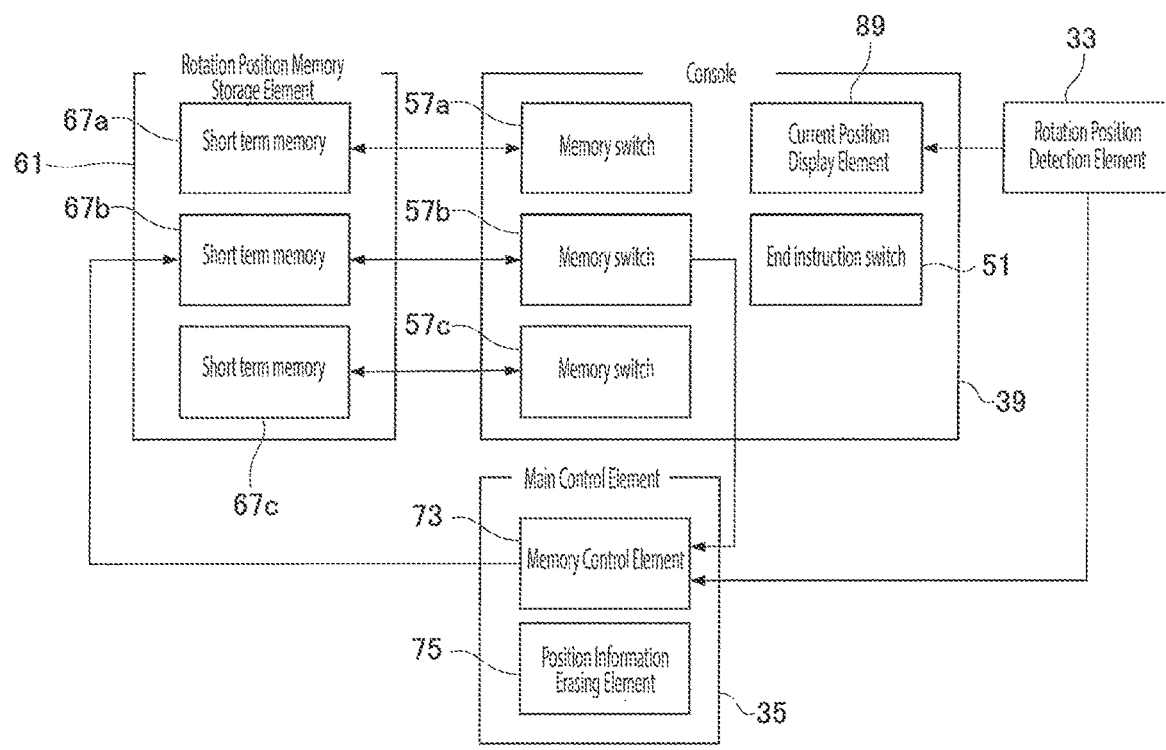
FIG. 19 is a schematic diagram illustrating the essential component of the X-ray fluoroscopic imaging apparatus at Step T3 according to the aspect of the Embodiment.

The operator pushes down the selected memory switches 57 following selection of the memory switches 57 (Step T3). Referring to FIG. 19, the memory switches 57 are pushed down and then the information of the rotation position of the C-arm 9, which the rotation position detection element 33 detects, are sent to the memory control element 73. In addition, the information identifying the short-term memory 67 in correspondence with the pushed-down memory switches 57 are sent to the memory control element 73.

The memory control element 73 registers the information of the rotation position of the C-arm 9 at the present time relative to the short-term memory 67 corresponding to the pushed-down memory switches 57 based on the received information. Specifically, the operator pushes down the memory switch 57b so that the information of the rotation position Fp is stored in the short-term memory 67b. Once the information of the rotation position Fp is registered, the information of the rotation position Fp instead of the additional information Rp is displayed in the memory switch 57b.

Figure 20:
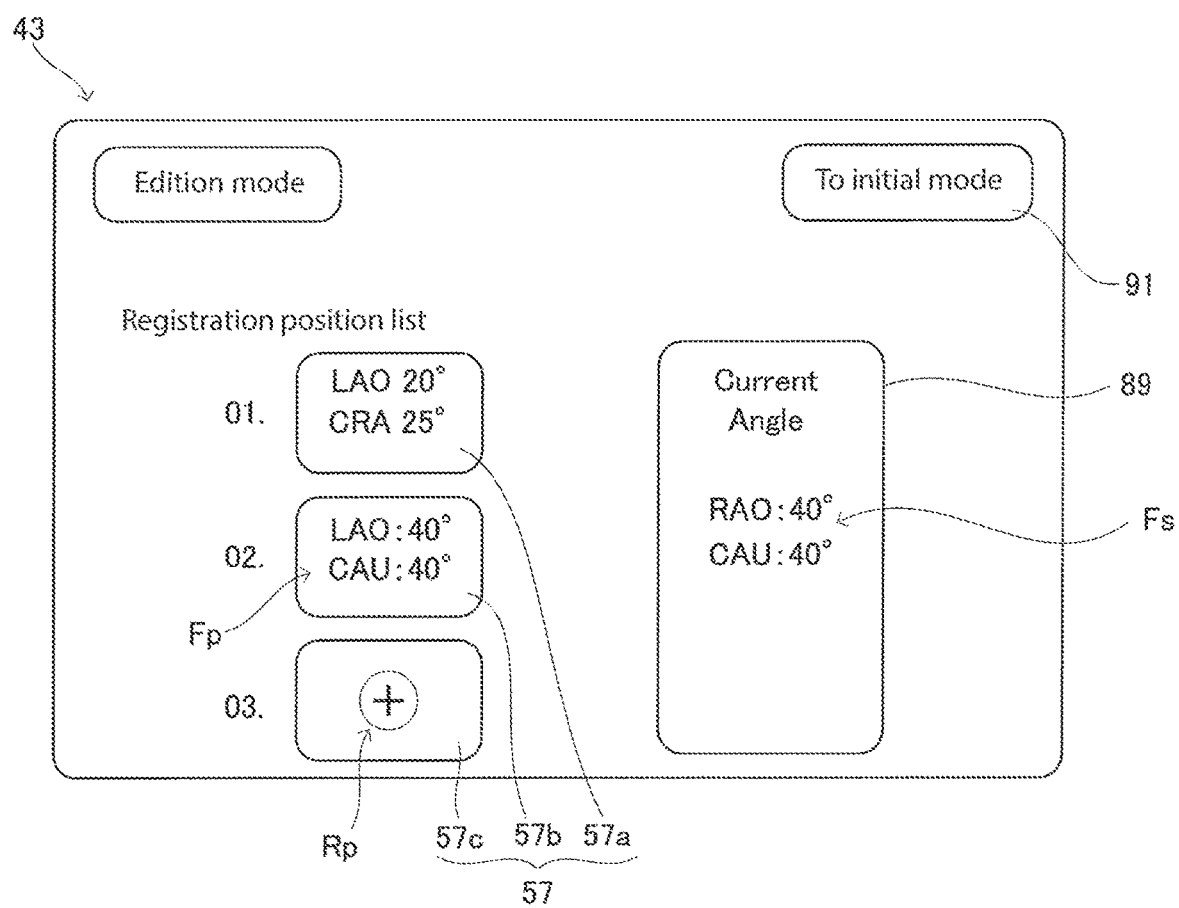
FIG. 20 is a view illustrating a touch panel display screen at Step T3 according to the Embodiment.

In addition, when the information of the rotation position Fs is registered in correspondence with the memory switches 57, the operator pushes down the memory switch 57c following rotating the C-arm 9 to the rotation position Fs. Referring to FIG. 20, the information of the rotation position Fs is displayed in the current position display element 89 due to rotating the C-arm 9 to the rotation position Fs. The information of the rotation position Fs that is the rotation position of the C-arm 9 at the present time are stored in the short-term memory 67c due to pushing down the memory switch 57c in the edition mode. Once the rotation position Fp and the rotation position Fs that are the targets to be registered are stored, the edition mode operation ends. Once the operator pushes down the mode return switch 91, the touch panel 43 returns to the default mode from the edition mode.

The operator alternatively shifts the C-arm 9 to the rotation position Fp and to the rotation position Fs by the auto-positioning operation following return to the default mode. Specifically, the operator pushes down the memory switch 57b while the touch panel 43 is in the state of the default mode (Step S1, S2). The additional information Sp is displayed in the memory switch 57b by pushing down the memory switch 57b and it is indicated that the memory switch 57b is in the selected state (Step S3). The rotation instruction switch 45 is pushed down in the state in which the additional information Sp is displayed in the memory switch 57b, by which the C-arm 9 rotates to the rotation position Fp (Step S4).

When the C-arm 9 rotates from the rotation position Fp to the rotation position Fs, the operator pushes down the memory switch 57c. And the rotation instruction switch 45 is pushed down in the state in which the additional information Sp is displayed in the memory switch 57c, by which the C-arm 9 rotates to the rotation position Fs. The operator alternatively rotates the C-arm 9 to the rotation position Fp and to the rotation position Fs by the auto-positioning operation while performing the X-ray fluoroscopy, so that the procedural operation can be quickly and adequately progressed referring to the X-ray image that is obtained by the X-ray fluoroscopy.

Figure 21:
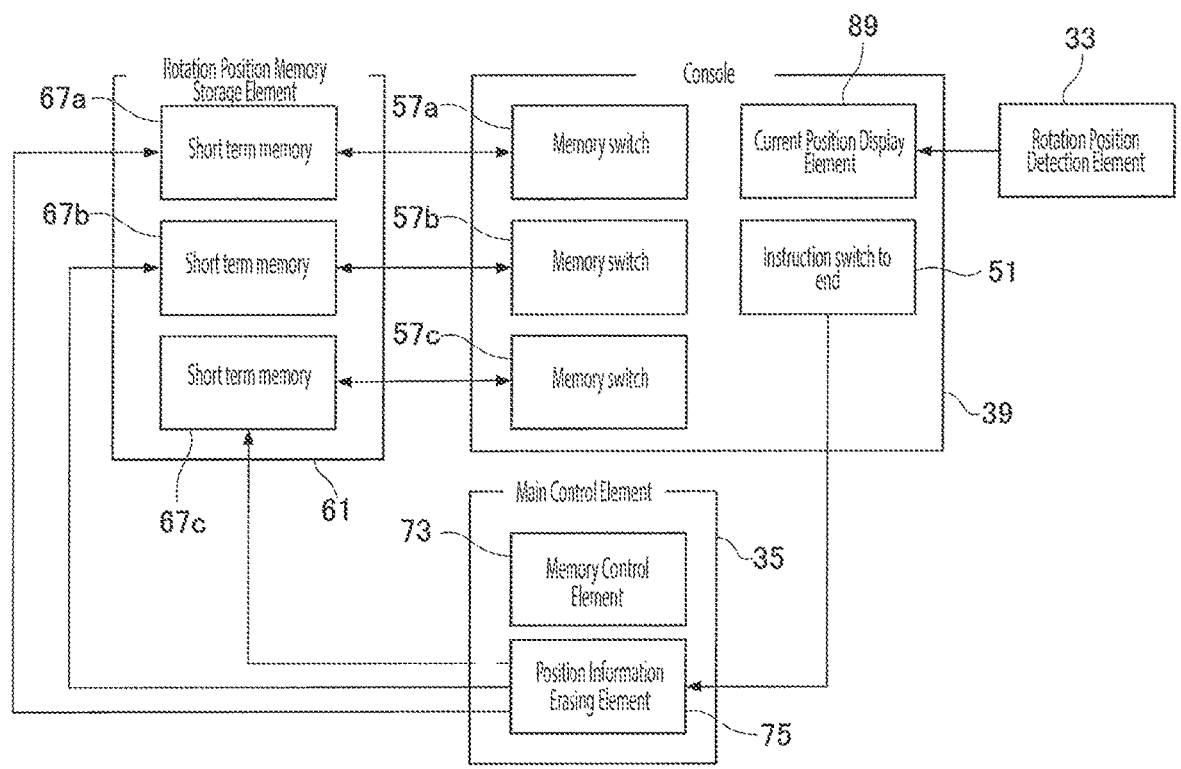
FIG. 21 is a functional block diagram illustrating the control mechanism of the information erase element according to the Embodiment.

When the procedural operation or the examination for the subject M ends, the operator pushed down the end instruction switch 47 installed to the console 39. Referring to FIG. 21, the position information erasing element 75 is activated by the operation for pushing down the end instruction switch 47 as the trigger. The position information erasing element 75 erases all information of the rotation position information stored in correspondence with the respective memory switches 57. Specifically, the position information erasing element 75 erases the respective rotation position information stored in the short-term memories 67a-67c.

The information of the rotation position Fp and the rotation position Fs is temporarily stored in the short-term memory 67 by using such an edition mode as far as the duration in which the procedural operation on the subject M is being performed. In addition, no operation on the registration instruction switch 83 and the confirmation key 87 are required in the edition mode, which is different from the registration mode. Specifically, the rotation position information displayed in the current position display element 89 are stored in the short-term memories 67 according to the simple operation in which the memory switches 57 corresponding to the short-term memories 67, in which the rotation position information is temporarily stored, are pushed down. Consequently, the edition mode to register on the second memory switch group M2 is applied, so that the necessary steps needed to register the rotation position can be cut down.

The end instruction switch 47 is mandatory to end the procedural operation for the subject M. Therefore, a series of operations required to end the procedural operation for the subject M is executed, and thereby the control to erase the information of the short-term memories 67a-67c can be absolutely executed with the operation of the end instruction switch 47 as the trigger. Therefore, the incident of forgetting to erase the information of the rotation position Fp and the rotation position Fs, which are important only in the procedural operation for the subject M, can be avoided.

The information of the rotation position Fp and the rotation position Fs is automatically erased when the procedural operation for the subject M ends, so that the unregistered state comes into which the rotation position information that is absolutely not registered in the respective short-term memories 67 corresponding to the respective memory switches 57 when the X-ray fluoroscopic imaging apparatus 1 is applied to the next different subject N. Consequently, it can be avoided that the operator hesitates to overwrite such short-term memories 67 with the rotation position information being registered due to remaining the past-registered information of the rotation positions in the short-term memories 67.

(Effects of the Aspect of Embodiment)

(Term) The X-ray fluoroscopic imaging apparatus 1 according to the present Embodiment comprises: an X-ray tube 5 that irradiates an X-ray to a subject M; an X-ray detector 7 that is in place facing the X-ray tube 5 detects the X-ray transmitting the subject M; a C-arm 9 that supports the X-ray tube 5 and the X-ray detector 7 to face each other and is rotatable around respective two axes that are orthogonal to each other; a rotation position detection element 33 that detects an information related to a rotation direction and a rotation angle around the respective axes of the C-arm 9 as rotation position information; a plurality of memory switches 55; a rotation position memory storage element 61 that stores the rotation position information in correspondence with any of memory switches 55; a touch panel 43 that displays the rotation position information that are stored in correspondence with such memory switches 55 selected by selection any of the memory switches 55; and a rotation instruction switch 45 that rotates the C-arm 9 in the rotation direction and with the rotation angle in correspondence with the rotation position information that is displayed in the touch panel 43, wherein the rotation position memory storage element 61 is configured to store a plurality of rotation position information in correspondence with the respective memory switches 55, and the touch panel 43 is configured to display any of the plurality of rotation position information stored in correspondence with the memory switches 55 in a predetermined display manner due to operating the memory switches 55 in the predetermined operation manner.

Figure 22:
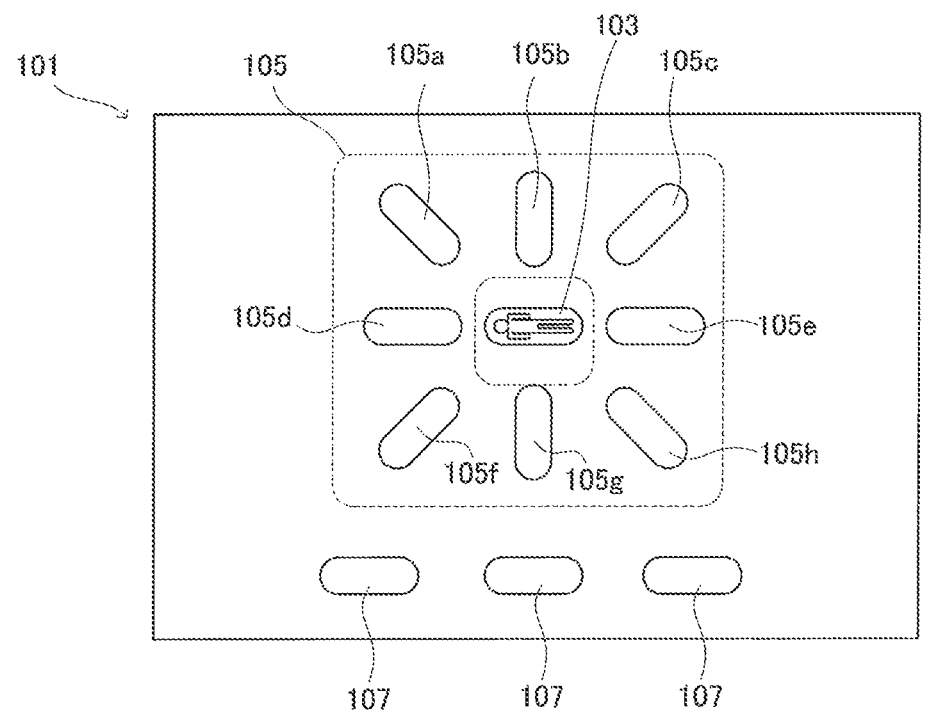
FIG. 22 is a plane view illustrating a structure of a console according to a conventional example.
Figure 23:
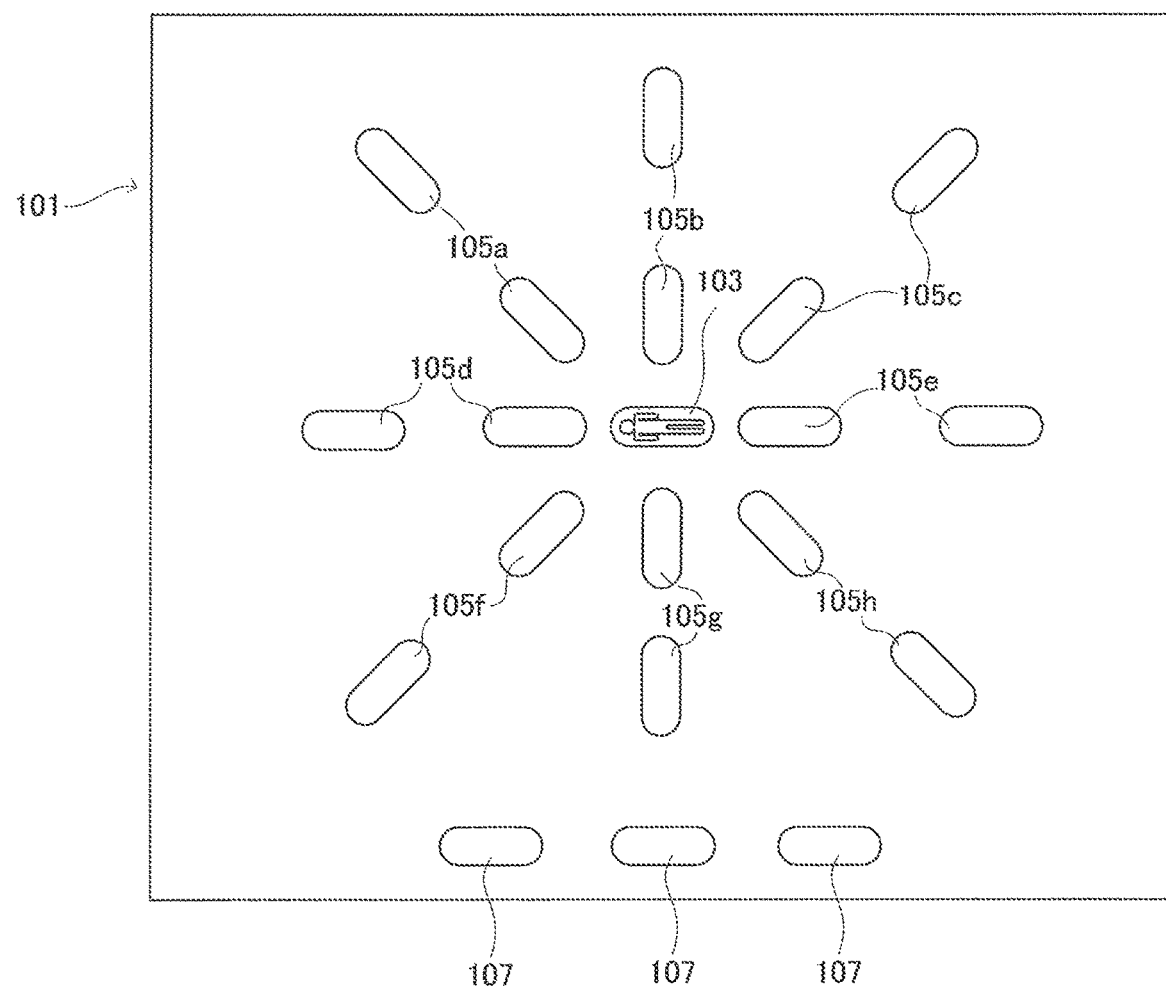
FIG. 23 is a plane view illustrating the problem of the operation panel of the conventional Embodiment.

Referring to FIG. 22 or FIG. 23 the inventors set forth an effect due to the fluoroscopic imaging apparatus 1 described in Term 1. FIG. 22 is a view illustrating a console 101 applied to a conventional X-ray fluoroscopic imaging apparatus.

The console 101 comprises a center switch 103 having a displayed humanoid symbol and eight memory switches 105 placed around the center switch 103. Each of the memory switches 105 is distinguished as the respective memory switches 105*a*-105*h* from one another. In addition, the console 101 comprises extra memory switches 107 that are reserved memory switches. The respective extra memory switches 107 are in place away from the center switch 103.

It is defined so that the positional relationship between the memory switches 105*a*-105*h* and the center switch 103 coincides with the positional relationship between the rotation position of the C-arm and the subject loaded on the table. Specifically, the rotation position toward LAO direction and CRA direction relative to the subject is stored in correspondence with the memory switch 105*a*, that is in place at the upper left side of the center switch 103.

The target memory switch 105 stored in correspondence with such a rotation position is decided in accordance with the positional relationship of the rotation position relative to the subject, so that the memory switch 105 to be selected on executing the auto-positioning operation can be intuitively understood. In addition, the rotation position toward the RAO direction and the CRA direction is stored in the memory switch 105 and after a while the auto-positioning for the C-arm 9 to such a rotation position may be performed. In such a case, it is intuitively understandable that such rotation position information is registered in advance in the memory switch 105*f* that is in place at the lower left side of the center switch 103.

Here, one rotation position information is stored in correspondence with one memory switch therefor when executing the auto-positioning operation using the conventional X-ray fluoroscopic imaging apparatus. Therefore, when more than two rotation positions toward the same direction are registered in advance, it is difficult to store the respective rotation positions in correspondence with the memory switches 105 to be intuitively understood.

For example, it is given that the information of the rotation position M1 for rotating in the LAO direction and the CRA direction is already stored in correspondence with the memory switch 105*a*. In such a scenario, the new information of the rotation position M2 for rotating in the LAO cannot be stored in correspondence with the memory switch 105*a*. In case of forcibly storing the information of the rotation position M2 in correspondence with memory switch 105*a*, at least the information of the rotation position M1 already stored is subject to be lost.

In addition, when executing the operation to overwrite the information of the rotation position M1 with the information of the rotation position M2 according to the conventional aspect, such an overwriting and registration operation is required to be the different operation therefrom in comparison with the operation in which the new rotation position information is registered for the memory switches 105 in which the rotation position information is not yet registered. For example, the operation for newly registering the rotation position is the operation in which the memory switches 105 are pushed down for a short period of time, whereas the operation for overwriting and registering needs a complex operation e.g., the operation in which the memory switches 105 are being pushed down for a long period of time or the memory switches 105 and the other switch are simultaneously pushed down. As a result, in the case of overwriting and registering, it is concerned that the operation may need a longer period of time, or an erroneous operation may take place.

According to the conventional configuration, when the information of the rotation position M2 is registered while storing the information of the rotation position M1, it is common that the operation for storing information of the rotation position M2 in correspondence with the extra switch 107 is executed. Whereas the positional relationship between the extra switch 107 and the center switch 103 is not reflected in the positional relationship between the subject and the rotation position M2.

Consequently, when the C-arm 9 rotates to the rotation position M2 again due to the auto-positioning operation following registration of the information of the rotation position M2, the operator may be confused about which switch should be selected to read out the information of the rotation position M2. As a result, it takes a longer time required for the auto-positioning operation, so that it is concerned that the progression of the quick procedural operation can be disturbed.

Such issues are particularly remarkable when the procedural operation due to auto-positioning operations is carried on a number of subjects. Specifically, the incident in which the predetermined rotation positions are registered may take place every procedural operation that is carried on the subject. Therefore, provided the procedural operation is carried on a number of subjects, the rotation position information is already registered in the predetermined memory switches 105, so that the incident in which no information of the new rotation position can be registered takes place promptly.

It is considered that such a configuration, in which a plurality of memory switches 105a-105h is in place, may be the solution for the problem as to an immediate occurrence of the incident in which no information of the new rotation position can be registered in the memory switches 105. Specifically, a plurality of the memory switches 105a is in place and a plurality of memory switches 105b-105h are also respectively in place.

However, provided multiple sets of the memory switches 105a-105h are in place while keeping the positional relationship with the center switch 103, the memory switches 105a-105h must be in place as illustrated in FIG. 23. Specifically, multiple sets of the memory switches 105a-105h are in place so as to expand radially from the center switch 103 as the center thereof, so that the console 101 must be made much larger to place all memory switches 105. As a result, it is concerned about the problem in which it is difficult to secure the installation space for the console 101.

Compared with the conventional configuration, the X-ray fluoroscopic imaging apparatus, according to Term 1 comprises the touch panel 43, a plurality of memory switches 55, the rotation position memory storage element 61 and the rotation instruction switch 45. The touch-panel 43 displays the rotation position information that is stored in correspondence with such memory switches 55 selected by selecting any of memory switches 55. The rotation position memory storage element 61 stores the rotation position information of the C-arm 9 in correspondence with any of the memory switches 55 and is configured to store a plurality of rotation position information corresponding to the respective memory switches 55. The touch-panel 43 is configured to display any of the plurality of rotation position information stored in correspondence with such memory switches 55 in the predetermined manner due to the operation of the memory switches 55 in the predetermined operation manner.

Specifically, the X-ray fluoroscopic imaging apparatus 1 is capable of storing every one memory switch 55 in correspondence with a plurality of rotation positions. Consequently, while lowering the number of the memory switches apparatus, a larger number of the rotation position information can be stored for a long time in correspondence with the memory switches 55.

A plurality of the rotation position information that is respectively stored in corresponding to each one of memory switches 55 can be displayed in the predetermined display manner by operating the memory switches 55 placed in the touch panel 43 in the predetermined operation manner. Specifically, the information of the respective rotation positions can be selectively read out and displayed corresponding to the operation manner of the memory switch 55 even when a plurality of the rotation positions is stored in correspondence with one memory switch 55.

And the C-arm 9 is capable of rotating in the rotation direction and with the rotation angle respectively corresponding to the rotation position information that is displayed in the touch-panel 43 due to the operation of the rotation switch 45. Accordingly, an operation is now achievable, wherein the C-arm 9 is rotated to such a rotation position by selecting the one rotation position from a plurality of stored rotation positions with regard to the configuration in which the plurality of the rotation positions are stored in correspondence with one memory switch 55.

Particularly, when the operation manner for the memory switches 55 is the number of pushing down the memory switches 55, one of the multiple rotation position information stored in correspondence with such memory switches 55 is displayed on the touch panel 43 in order. Once the desired rotation position information is displayed on the touch panel 43, the operator can rotate the C-arm 9 to such a rotation position by operating the rotation instruction switch 45. In such a case, the auto-positioning operation in which the C-arm 9 rotates to the desired rotation position can be brought in reality by a simple operation, i.e., pushing down the respective switches. Specifically, no complex operation e.g., the operation of pushing down a switch for a long time or the operation of simultaneously pushing down a plurality of switches, is required, so that the auto-positioning operation can be executed exactly in a short period of time.

(Term 2) In addition. the X-ray fluoroscopic imaging apparatus according to Term 1, the respective memory switches 55 are in place at the position corresponding to the rotation direction stored in correspondence with the memory switches as the basis for the reference region indicating the position of the subject M.

With regard the X-ray fluoroscopic imaging apparatus according to Term 2, the position, at which the respective memory switches 55 are in place on the basis of the center switch 53, is defined so as to correspond to the direction of the rotation position stored in correspondence with the memory switches 55 on the basis of the rotation position F0 stored in correspondence with the center switch 53.

According to such a configuration, based on the direction in which the memory switches 55 are in place on the basis of the position at which the center switch 53 is in place, the operator can intuitively understand that the rotation position stored in correspondence with such memory switches 55 is in which direction on the basis of the initial rotation position F0 in correspondence with the center switch 53. Therefore, the time needed for the auto-positioning operation can be reduced, and an incident of an error operation during the auto-positioning operation can be absolutely avoided.

For example, the memory switches 55h are in place at the lower right side of the center switch 51. Consequently, the operator can intuitively understand that the information of the rotation position that rotates in the lower right direction, i.e., the RAO direction and the CAU direction on basis of the initial rotation position F0 is stored in the memory switch 55h in correspondence therewith. Therefore, the operator can quickly select the switch, in which the information of the target rotation position is stored in correspondence therewith, from a plurality of memory switches 55a-55h. In addition, when newly registering the information of the rotation position, the operator can quickly select the memory switches 55 that are the targets to be stored in correspondence with such information of the rotation position.

(Term 3) The X-ray fluoroscopic imaging apparatus according to the second aspect of the present Embodiment comprises: an X-ray tube 5 that irradiates an X-ray to a subject; an X-ray detector 7 that is in place facing the X-ray tube 5 detects the X-ray transmitting the subject M; a C-arm 9 that supports the X-ray tube 5 and the X-ray detector 7 to face each other and is rotatable around respective two axes that are orthogonal to each other; a rotation position detection element 33 that detects information related to a rotation direction and a rotation angle around the respective axes of the C-arm 9 as rotation position information; a plurality of memory switches 57; a rotation position memory storage element 61 that stores the rotation position information in correspondence with any of memory switches 57; a touch panel 43 that displays the rotation position information that are stored in correspondence with such memory switches 57 selected by selection any of the memory switches 57; and a rotation instruction switch 45 that rotates the C-arm in the rotation direction and with the rotation angle in correspondence with the rotation position information that are displayed in the touch panel 43; and a position information erasing element 75 that erases the rotation position information stored in correspondence with the respective memory switches 57 due to the operation as a trigger that instructs the specific step specified in advance in a series of examination steps relative to the subject M.

The X-ray fluoroscopic imaging apparatus, according to Term 3, comprises the touch panel 43, a plurality of memory switches 57, the rotation position memory storage element 61, the rotation instruction element 45 and the rotation position information erasing element 75. The touch panel 43 displays the rotation position information that is stored in correspondence with such memory switches 57 selected by selecting any of memory switches 57. The rotation position memory storage element 61 stores the rotation position information of the C-arm 9 in correspondence with any of the memory switches 57.

Once the desired rotation position information stored in correspondence with such memory switches 57 is displayed on the touch panel 43, the operator selects the memory switches 57, and rotates the C-arm 9 to such a rotation position by operating the rotation instruction switch 45. In such a case, the auto-positioning operation in which the C-arm 9 rotates to the desired rotation position can be brought in reality by a simple operation, i.e., pushing down the respective switches. Specifically, no complex operation e.g., the operation of pushing down a switch for a long time or the operation of simultaneously pushing down a plurality of switches, is required, so that the auto-positioning operation can be executed exactly in a short period of time.

And once the operation for instructing a specific predetermined process of a series of examination processes relative to the subject M is performed, the rotation position information erasing element 75 erases the rotation position information stored in correspondence with the respective memory switches 57 using such an operation as a trigger. In such a configuration, once a series of examination processes relative to the subject M is completed, the rotation position information stored in correspondence with the respective memory switches 57 are automatically erased. In other words, the memories of the rotation position information in correspondence with the memory switches 57 are temporary or stored in a short period of time. Specifically, the rotation position information stored in correspondence with the memory switches 57 when the examination is carried on the subject are stored only as far as the duration in which the examination is ongoing on such a subject.

Consequently, at the time when the examination for a new subject starts, no information of the rotation position stored while the examination for the previous subject is carried on are left in the memory switches 57. Therefore, the incident in which the operation is incapable of storing the new rotation position information in correspondence with such memory switches 57 or the incident of hesitation in the operation to store due to remaining the rotation position information stored during the past examination in the memory switches 57 can be avoided.

In such a way, even when a number of rotation positions are needed to be stored since a number of subjects are examined, the information of the rotation positions is erased whenever the examination relative to the subject ends. Therefore, it is not required to forever and continuously store the rotation position information with regard to all subjects in correspondence with the respective individual memory switches 57. Specifically, the number of the memory switches 57 is limited to the number of the rotation positions to be stored mandatory with regard to the examination relative to each subject. Therefore, while reducing the number of the memory switches 57 installed to the X-ray fluoroscopic imaging apparatus 1, the examination for a number of subjects can be adequately performed using the auto-positioning operation.

(Term 4) In addition, the X-ray fluoroscopic imaging apparatus according to Term 3 comprises an edition shifting switch 51 that executes shilling to the edition mode to store the rotation position information in the memory switches 51 by the rotation position memory storing element 61, wherein the rotation position memory storing element 61 stores the rotation direction and the rotation angle of the C-arm 9 as the rotation position information in correspondence with the memory switches 57 by operating any of the memory switches 57 in the state of shifting to the edition mode.

According to the X-ray fluoroscopic imaging apparatus described in Term 4, the rotation position memory storing element 61 stores the rotation direction and the rotation angle of the C-arm 9 at the time when the operation is executed in correspondence with the memory switches 57 as the rotation position information by operating any of the memory switches 57. Therefore, once it is found that the desired X-ray image is obtained by the X-ray fluoroscopic imaging, the rotation position information of the C-arm 9, at the time when the X-ray image is obtained, is automatically stored by operating the memory switches 57. Specifically, the rotation position information corresponding to the X-ray image imaging condition is exactly and quickly stored, so that the rotation position of the C-arm 9 required to obtain such an X-ray image can be easily and precisely reproduced later.

(Term 5) In addition, the X-ray fluoroscopic imaging apparatus, according to any one term of Term 1 to Term 4, comprises the display control element 71 displays the latest memory switch operated by the operator among a plurality of memory switches in a different manner from other memory switches.

According to the X-ray fluoroscopic imaging apparatus of Term 5, the latest memory switches 55 (or memory switches 57) operated by the operator are displayed in the different manner from other memory switches 55 (or memory switches 57) by the display control element 71. In such a configuration, the operator can absolutely identify the latest operated memory switch from a plurality of the memory switches. Therefore, an erroneous operation in the auto-positioning, operation can be avoided and the time needed for such an operation can be further shortened, Other Embodiments Specifically, the aspects of the Embodiment disclosed at this time are examples and not limited thereto in any points. The scope of the present invention includes the claims and all alternatives and equivalents thereof within the scope thereof. For example, the present invention can be implemented in the below alternative Embodiment.

(1) According to Embodiment set forth above, the console 39 comprises the first memory switch group M1 and the second memory switch group M2, but not limited thereto. Specifically, the console 39 may comprise only the first memory switch group M1 instead of both first memory switch group M1 and second memory switch group M2, or only the second memory switch group M2 instead of both thereof.

(2) In the above Embodiments or the alternative Embodiment, for example, the configuration in which the direct registration mode and the manual registration mode is selectively applied in the registration mode using the first memory switch group M1 is disclosed, but only either one mode may be applied. In addition, in the edition mode using second memory switch group M2, Embodiment using only i.e., the direct registration mode in which the rotation position information of the C-arm 9 at the present, time is stored every time when the memory switches 57 are pushed down is illustrated, but not limited thereto. Specifically, the manual registration mode may be selected even in the edition mode.

(3) In the above Embodiments or the alternative Embodiment, the components of a variety of switches installed to the console 39 may be arbitrarily modified and arbitrarily changed to e.g., such as an icon displayed on the touch panel, a dial-type switch or a pushbutton switch.

Figure 24:
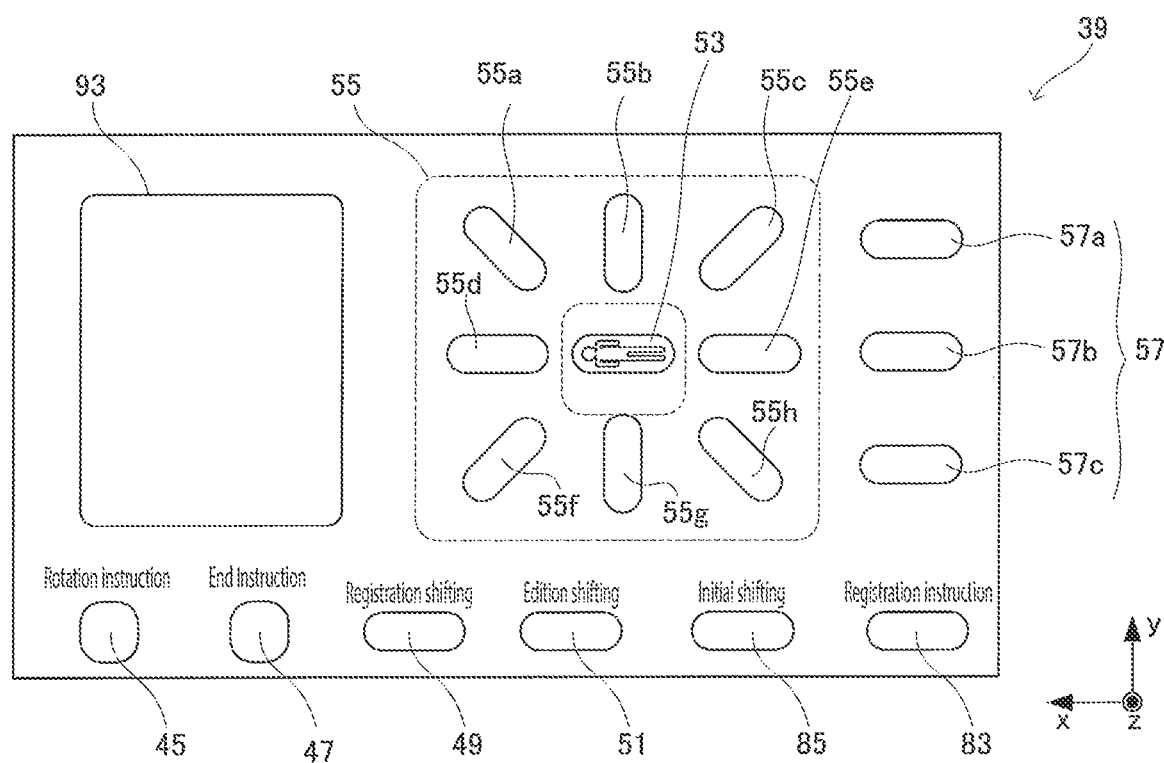
FIG. 24 is a plane view illustrating a structure of the console according to the alternative Embodiment.
Figure 25:
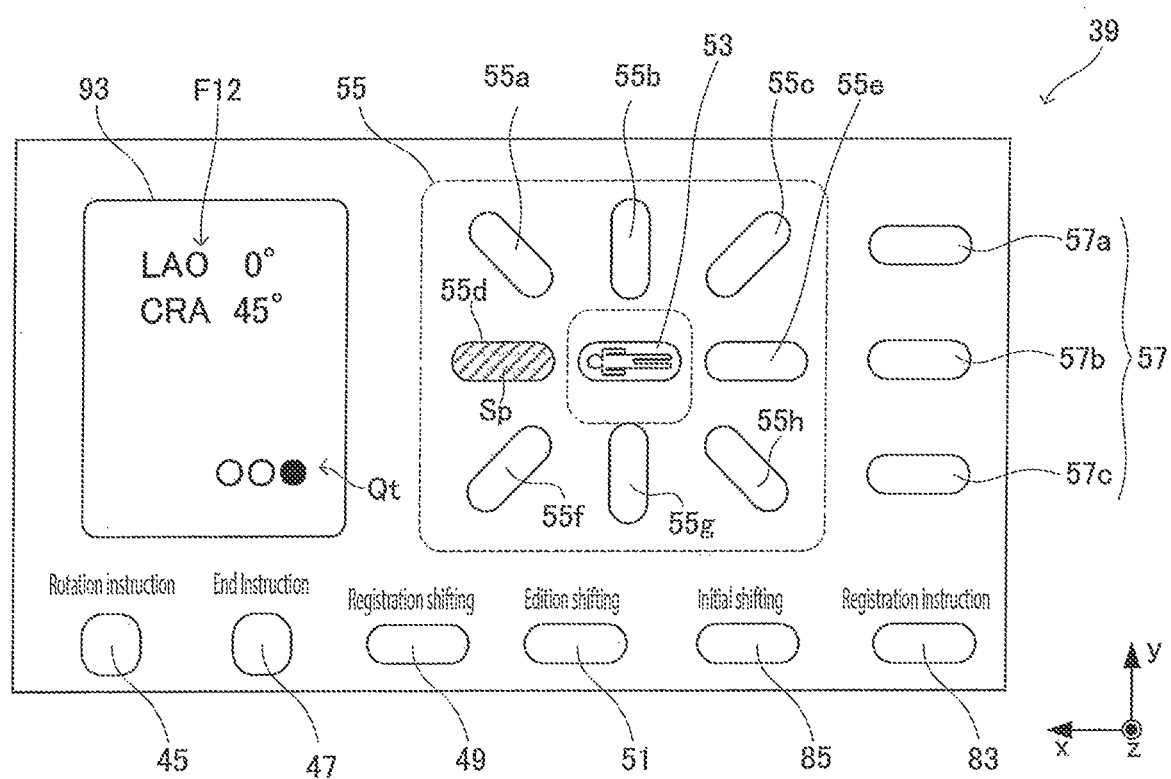
FIG. 25 is a plane view illustrating Step S3 according to the alternative Embodiment.

FIG. 24 is a schematic diagram illustrating an example of the console 39 of an alternative Embodiment. In the console 39 of the alternative Embodiment, the center switch 53, the memory switches 55 and the memory switches 57 are all pushbutton switches. Specifically, the console 39 of the alternative Embodiment has not the touch panel 43.

In addition, the console 39 of the alternative Embodiment comprises a rotation position display monitor 93. The rotation position display monitor 93 displays such as the information of the rotation position read out by the read-out element 69 due to pushing down the memory switches 55 or the memory switches 57 and a variety of additional information added by the display control element 71. In the console 39 of the alternative Embodiment, a variety of switches such as the registration shifting switch 49, the edition shifting switch 51, the registration instruction switch 83, the mode returning switch 85 are also pushbutton switches.

The inventors set forth the operation using the console 39 according to the alternative Embodiment. For example, the operator pushes down the memory switch 55d three times when executing an auto-positioning operation to the rotation position F12 in the default mode. Due to such push-down operation, the read-out element 69 reads out the information of the rotation position F12 from the third memory switch 65d and the display control element 71 displays such rotation position information along with the additional information Qt on the rotation position display monitor 93. In addition, the display control element 71 displays the additional information Sp relative to the memory switch 55d.

In the alternative Embodiment, the additional information Sp is the information that instructs displaying the latest selected memory switch 55d in the different color from other memory switches 55 thereof. The operator confirms the information of the rotation position F12 displayed on the rotation position display monitor 93 and then pushes down the rotation instruction switch 45. The C-arm 9 rotates to the rotation position F12 due to the operation for pushing down the rotation instruction switch 45.

In such a way, even if the console 39 does not have the touch panel 43, the operation related to the respective modes can be executed using a variety of switches and the rotation position display monitor 93.

(4) In the Embodiments or the alternative Embodiment set forth above, the center switch 53 is configured to be capable of storing in correspondence with only one rotation position but may be configured to be capable of storing a plurality of the rotation positions as well as the memory switches 55.

(5) In the Embodiments or the alternative Embodiment set forth above, the operation as the trigger for the position information erasing element 75 to be activated is illustrated as e.g., pushing down the end instruction switch 51 to end the procedural operation for the subject M, but not limited thereto. For the other example, an operation of turning on or off the main power source for the X-ray fluoroscopic imaging apparatus 1 or an operation of activating the position information erasing element 75 may be applied to the trigger to start the procedural operation for the subject M. Specifically, any mandatory operation in a series of the operations to complete the procedural operation for the subject M can be arbitrarily applied to such a trigger.

(6) In the Embodiments or the alternative Embodiment set forth above, the respective memory switches 55a-55h are in correspondence with three memories 63-65 and three rotation positions can be registered as a maximum. Regardless, the maximum number of the rotation position registrable to the respective memory switches 55a-55h is not limited to three and may be arbitrarily changed. Specifically, the number of the registrable rotation positions can be arbitrarily adjusted by arbitrarily changing the number of memories in correspondence with the memory switches 55. In addition, the maximum number of the registrable rotation positions is not limited to be the same as for all memory switches 55a-55h. For example, the memory switch 55a is configured to have the two registrable rotation positions as a maximum, and on the other hand the memory switch 55g may be configured to have the four registrable rotation positions as a maximum.

(7) In the Embodiments or the alternative Embodiment set forth above, the operation of pushing down the memory switches 57 that are targets for the registration operation following switching the default mode referring to FIG. 10 to the edition mode referring to FIG. 18 is illustrated as the method of registering the information of the rotation position of the C-arm 9 in the memory switches 57, but not limited thereto. For example, the configuration in which the rotation position information is registered by pushing down the memory switches 57 in the default mode state referring to FIG. 10 may be adopted.

For a specific example, in the default mode state, the information of the rotation position of the C-arm 9 at the time when such push-down operation is executed is stored in correspondence with the memory switch 57b by pushing down the memory switch 57b to which the additional information Rp is added. Providing the rotation position information to be registrable to the memory switches 57 in the default mode, the operation for registering the rotation position in the memory switches 57 can be further simplified.

(8) In the Embodiments or the alternative Embodiment set forth above, it is illustrated that the additional information Qt includes e.g., the information identifying the number of the rotation positions registered in the memory switches 55 but also may include the information indicating the number of the memories 63-65 in correspondence with the memory switches 55. Specifically, in Embodiment, the number of the circular symbols consisting of the additional information Qt indicates the number of the rotation positions registered in the memory switches 55 at the present time. Instead, the number of the circular symbols consisting of the additional information Qt may indicate the number of the memories 63-65 in correspondence with the memory switches 55 (upper limit number of the rotation positions registrable in the memory switches 55).

REFERENCE OF SIGNS

1. X-ray fluoroscopic imaging apparatus
3 Table
5 X-ray tube
7 X-ray detector
9 C-arm (support mechanism)
17 Collimator
29 X-ray irradiation control element
30 Image generation element
31 image display element
33 Rotation position detection element
35 Main control element
37 Memory storage element
39 Console
41 Arm operation lever
43 Touch panel
45 Rotation instruction switch (Rotation instruction element)
47 End instruction switch
49 Registration shifting switch
51 Edition shifting switch
53 Center switch
55 Memory switch
57 Memory switch
61 Rotation position memory storage element
63 First memory
64 Second memory
65 Third memory
67 Short term memory
69 Read-out element
71 Display control element (Selected memory switch display mechanism)
73 Memory control element
75 Position information erasing element (Rotation position information erasing element)
77 Memory selection switch
79 Present position display element
83 Registration instruction switch
85 Mode return switch
89 Present position display element
91 Mode return switch
93 Rotation position display monitor Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they conic within the scope of the appended claims and their equivalents.

What is claimed is:

1. An X-ray fluoroscopic imaging apparatus, comprising:
an X-ray tube that irradiates an X-ray toward a subject;
an X-ray detector that is in place facing said X-ray tube detects said X-ray transmitting said subject;
a support mechanism that supports said X-ray tube and said X-ray detector so as to face each other and is rotatable around each of a first axis and a second axis that are orthogonal to each other;
a plurality of memory switches;
a rotation position memory storage element, that stores a rotation position information that is a combination of information on the rotation direction and rotation angle around said first axis and information on the rotation direction and rotation angle around said second axis in correspondence with respective said plurality of memory switches;
a rotation position display element that displays said rotation position information in a manner that allows identification of which memory switch among said plurality of memory switches the rotational position information is stored in correspondence with; and;
a rotation instruction element that rotates the support mechanism to a position corresponding to the rotation position information stored in correspondence with the memory switch operated by an operator;
wherein said rotation position memory storage element stores a plurality of said rotation position information in correspondence with said respective plurality of memory switches, and said rotation position information display element displays any of said plurality of rotation position information that is stored in correspondence with said memory switches that are operated in a predetermined display manner so that said memory switches are operated in a predetermined operation manner.

2. The X-ray fluoroscopic imaging apparatus, according to claim 1, wherein:
said respective plurality of memory switches are in place at a position corresponding to said rotation direction that is stored in correspondence with said memory switches based on a reference region indicating a position of said subject.

3. An X-ray fluoroscopic imaging apparatus, comprising:
an X-ray tube that irradiates an X-ray toward a subject;
an X-ray detector that is in place facing said X-ray tube detects said X-ray transmitting said subject;
a support mechanism that supports said X-ray tube and said X-ray detector so as to face each other and is rotatable around each of a first axis and a second axis that are orthogonal to each other;
a plurality of memory switches;
a rotation position memory storage element that stores a rotation position information that is a combination of information on the rotation direction and rotation angle around said first axis and information on the rotation direction and rotation angle around said second axis in correspondence with any of said memory switches;
a rotation position display element that displays said rotation position information in a manner that allows identification of which memory switch among said plurality of memory switches the rotational position information is stored in correspondence with;
a rotation instruction element that rotates the support mechanism to a position corresponding to the rotation position information stored in correspondence with the memory switch operated by an operator; and
a rotation position information erasing element that erases said rotation position information stored in correspondence with said respective memory switches as a trigger that is an operation instructing a predetermined specific process of a series of examination processes relative to said subject.

4. The X-ray fluoroscopic imaging apparatus; according to claim 3, further comprising:
a memory mode shifting instruction element that shifts a current mode to a memory mode in which said rotation position memory storage element stores said rotation position information in said memory switches,
wherein said rotation position memory storage element stores said rotation direction and said rotation angle of said support mechanism, at a time when an operation is executed, in correspondence with said memory switches as said rotation position information by operating any of said memory switches in a state shifted to said memory mode.

5. The X-ray fluoroscopic imaging apparatus, according to claim 1, further comprising:
a selected memory switch display mechanism that displays a latest memory switch operated by an operator among said plurality of memory switches in a different manner from a manner applied to said other memory switches.

6. An X-ray fluoroscopic imaging apparatus, comprising:
an X-ray tube that irradiates an X-ray toward a subject;
an X-ray detector that is in place facing said X-ray tube detects said X-ray transmitting said subject;
a support mechanism that supports said X-ray tube and said X-ray detector so as to face each other and is rotatable around respectively each of a first axis and a second axis that are orthogonal to each other;
a plurality of memory switches;
a rotation position memory storage element that stores a rotation position information that is a combination of an information on the rotation direction and rotation angle around said first axis and an information on the rotation direction and rotation angle around said second axis in correspondence with respective said plurality of memory switches; and
a rotation instruction element that rotates the support mechanism to a position corresponding to the rotation position information stored in correspondence with the memory switch operated by an operator,
wherein said rotation position memory storage element stores a plurality of said rotation position information in correspondence with said respective plurality of memory switches.

* * * * *